(12) United States Patent
Curran et al.

(10) Patent No.: US 7,905,886 B1
(45) Date of Patent: Mar. 15, 2011

(54) SYSTEM AND METHODS FOR PERFORMING TRANSFORAMINAL LUMBAR INTERBODY FUSION

(75) Inventors: Matthew Curran, Carlsbad, CA (US); Troy Woolley, San Diego, CA (US); Patrick Miles, San Diego, CA (US)

(73) Assignee: Nuvasive Inc., San Diego, CA (US)

( * ) Notice: Subject to any disclaimer, the term of this patent is extended or adjusted under 35 U.S.C. 154(b) by 0 days.

(21) Appl. No.: 10/887,542

(22) Filed: Jul. 7, 2004

Related U.S. Application Data

(60) Provisional application No. 60/485,559, filed on Jul. 7, 2003.

(51) Int. Cl.
*A61B 17/60* (2006.01)
*A61F 2/00* (2006.01)
(52) U.S. Cl. .......................................... 606/99
(58) Field of Classification Search ............ 606/61, 606/69–70, 86, 99; 623/17.11–16
See application file for complete search history.

(56) References Cited

U.S. PATENT DOCUMENTS

| | | | | |
|---|---|---|---|---|
| 5,339,801 A * | 8/1994 | Poloyko et al. | ............... | 600/214 |
| 5,341,707 A * | 8/1994 | Bond | ............... | 81/436 |
| 5,573,529 A * | 11/1996 | Haak et al. | ............... | 606/1 |
| 5,857,995 A * | 1/1999 | Thomas et al. | ............... | 604/22 |
| 6,174,311 B1 * | 1/2001 | Branch et al. | ............... | 606/61 |
| 6,261,296 B1 * | 7/2001 | Aebi et al. | ............... | 606/90 |
| 6,440,170 B1 * | 8/2002 | Jackson | ............... | 623/17.16 |
| 6,524,318 B1 * | 2/2003 | Longhini et al. | ............... | 606/86 |
| 6,663,562 B2 * | 12/2003 | Chang | ............... | 600/219 |
| 6,852,126 B2 * | 2/2005 | Ahlgren | ............... | 623/17.11 |
| 6,923,814 B1 * | 8/2005 | Hildebrand et al. | ............... | 606/99 |
| 2001/0010833 A1 * | 8/2001 | Ray et al. | ............... | 427/180 |
| 2002/0019637 A1 * | 2/2002 | Frey et al. | ............... | 606/85 |
| 2003/0135275 A1 * | 7/2003 | Garcia et al. | ............... | 623/17.11 |
| 2004/0143332 A1 * | 7/2004 | Krueger et al. | ............... | 623/17.14 |

* cited by examiner

*Primary Examiner* — Anu Ramana
(74) *Attorney, Agent, or Firm* — Nuvasive Inc.; Jonathan Spangler

(57) ABSTRACT

Systems and methods relating generally to spinal implants and insertion devices, and in particular, to intervertebral implant insertion devices, implants, and methods for performing transforaminal lumbar interbody fusion (TLIF).

17 Claims, 37 Drawing Sheets

| SIZE TABLE 1 | |
|---|---|
| DESCRIPTION | DIMENSION H |
| TLIF ALLOGRAFT 6 X 9 X 20mm | .276 |
| TLIF ALLOGRAFT 8 X 9 X 20mm | .355 |
| TLIF ALLOGRAFT 10 X 9 X 20mm | .433 |
| TLIF ALLOGRAFT 12 X 9 X 20mm | .512 |
| TLIF ALLOGRAFT 14 X 9 X 20mm | .591 |
| TLIF ALLOGRAFT 16 X 9 X 20mm | .670 |

| SIZE TABLE 2 | |
|---|---|
| DESCRIPTION | DIMENSION H |
| TLIF ALLOGRAFT 6 X 11 X 20mm | .276 |
| TLIF ALLOGRAFT 8 X 11 X 20mm | .355 |
| TLIF ALLOGRAFT 10 X 11 X 20mm | .433 |
| TLIF ALLOGRAFT 12 X 11 X 20mm | .512 |
| TLIF ALLOGRAFT 14 X 11 X 20mm | .591 |
| TLIF ALLOGRAFT 16 X 11 X 20mm | .670 |

| SIZE TABLE 3 | |
|---|---|
| DESCRIPTION | DIMENSION H |
| TLIF ALLOGRAFT 6 X 9 X 25mm | .276 |
| TLIF ALLOGRAFT 8 X 9 X 25mm | .355 |
| TLIF ALLOGRAFT 10 X 9 X 25mm | .433 |
| TLIF ALLOGRAFT 12 X 9 X 25mm | .512 |
| TLIF ALLOGRAFT 14 X 9 X 25mm | .591 |
| TLIF ALLOGRAFT 16 X 9 X 25mm | .670 |

| SIZE TABLE 4 | |
|---|---|
| DESCRIPTION | DIMENSION H |
| TLIF ALLOGRAFT 6 X 11 X 25mm | .276 |
| B TLIF ALLOGRAFT 8 X 11 X 25mm | .355 |
| TLIF ALLOGRAFT 10 X 11 X 25mm | .433 |
| TLIF ALLOGRAFT 12 X 11 X 25mm | .512 |
| TLIF ALLOGRAFT 14 X 11 X 25mm | .591 |
| TLIF ALLOGRAFT 16 X 11 X 25mm | .670 |

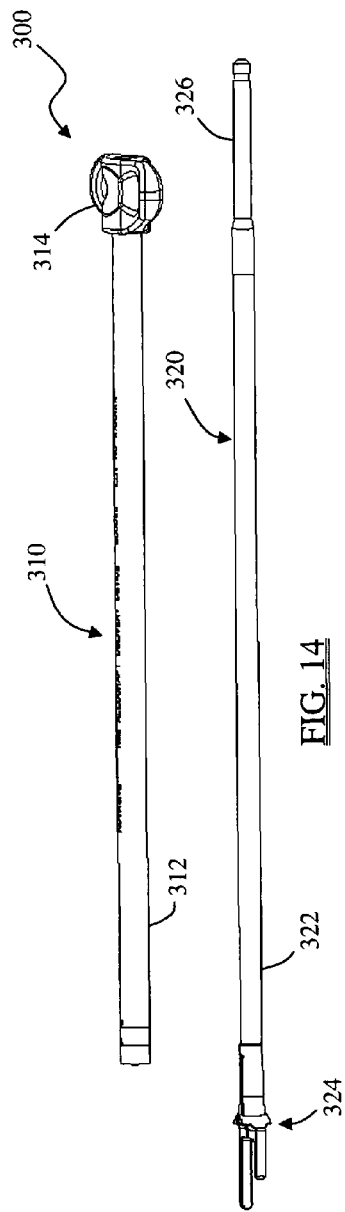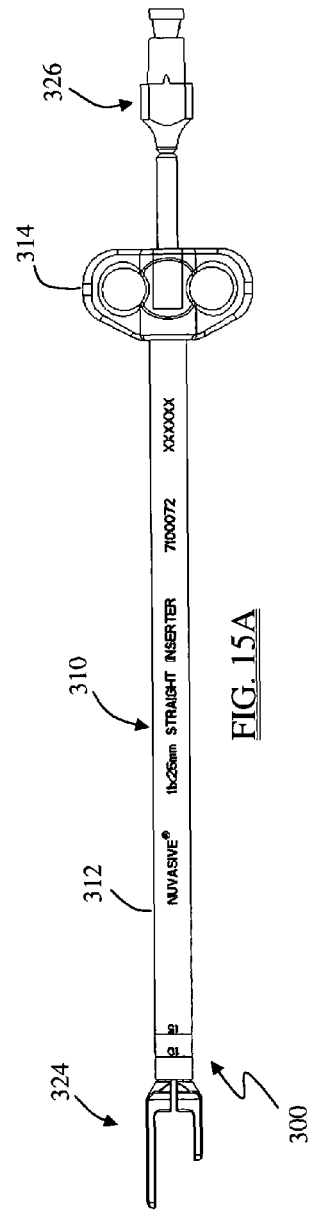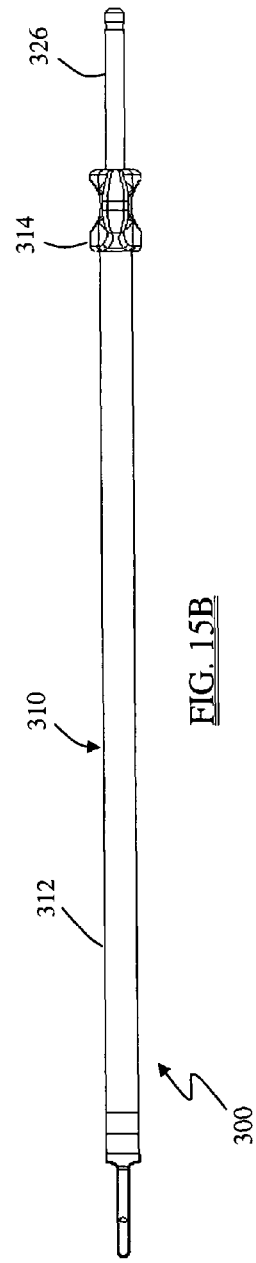
FIG. 14
FIG. 15A
FIG. 15B

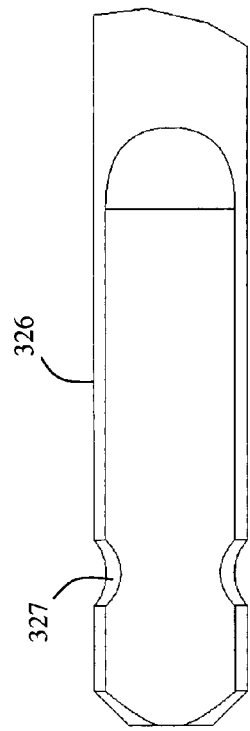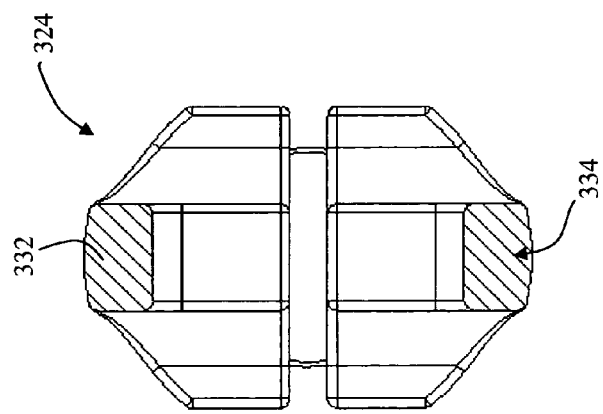
FIG.16E
FIG.16F

SYSTEM AND METHODS FOR PERFORMING TRANSFORAMINAL LUMBAR INTERBODY FUSION

CROSS REFERENCES TO RELATED APPLICATIONS

The present non-provisional patent application claims priority to commonly owned U.S. Provisional Patent Application Ser. No. 60/485,559 filed Jul. 7, 2003, the complete disclosure of which is hereby incorporated herein by reference in its entirety for all purposes.

BACKGROUND OF THE INVENTION

I. Field of the Invention

This invention relates generally to spinal surgery and, more particularly, to intervertebral implant insertion devices, implants, and methods for performing transforaminal lumbar interbody fusion (TLIF).

II. Description of the Related Art

In the area of spinal surgery, various techniques have been developed over time to fuse adjacent vertebral bodies together. One technique is so-called anterior lumbar interbody fusion (ALIF), which involves accessing the intervertebral space from a generally anterior approach and introducing one or more intervertebral implants such that the implants are positioned generally along the anterior region of the disc space. While generally effective at restoring disc height and promoting fusion between adjacent vertebral bodies, the ALIF technique has certain drawbacks, including the need for an additional surgeon in the operating room to gain access to the anterior aspect of the spine, and the inability to perform decompression.

To overcome the drawbacks or limitations of ALIF procedures, surgeons may employ the so-called posterior lumbar interbody fusion (PLIF) technique, which involves accessing the intervertebral space in a bilateral fashion from a generally posterior approach and introducing an intervertebral implant through each bilateral opening such that the implants are positioned along the lateral aspects of the disc space. PLIF is advantageous over ALIF in that it provides the ability to perform decompression and avoids the need for an access surgeon as required in ALIF procedures. However, notwithstanding these improvements, PLIF nonetheless suffers certain limitations, including the need to create two openings into the disc space (which causes muscle disruption bilaterally) and the need to retract the dura in order to access the disc space through each of the bilateral openings.

To overcome the drawbacks or limitations of PLIF procedures, surgeons have devised a still further technique, so-called transforaminal lumbar interbody fusion (TLIF), which involves accessing the spine in a unilateral fashion from a generally posterior approach and introducing one or more intervertebral implants into the generally anterior region of the disc space. This is accomplished by removing part or all of a single facet joint on one side of the spine, which thereby creates a channel through which to access the intervertebral disc. TLIF is advantageous over PLIF in that TLIF, by creating an access channel via facet removal, does not require the dura retraction as found in PLIF procedures. Also, by accessing the disc space in a unilateral fashion, TLIF minimizes the muscle disruption, as compared with the bilateral muscle disruption as found in PLIF procedures.

SUMMARY OF THE INVENTION

The present invention is directed at a system and methods for performing transforaminal lumbar interbody fusion. The system of the present invention may include any number of devices for performing transforaminal lumbar interbody fusion, including but not limited to a variety of TLIF implants, implant inserters for inserting the TLIF implants into the intervertebral space, positioning devices for positioning the TLIF implants after insertion, and packing devices for packing additional materials within the disc space to promote fusion. Optional preparation devices may also be provided for preparing the intervertebral space prior to implant insertion.

In use, access must first be gained to the disc space between vertebrae of interest. According to the TLIF procedure, this may be accomplished from a generally posterior approach to the patient's spine via a unilateral opening in the annulus of the intervertebral disc of interest. This may be accomplished in a traditional "open" manner (via a large incision) or, according to a preferred embodiment, in a minimally invasive fashion using a retractor or similar minimally invasive instrument, such as a cannula. Once accessed, the disc space must be prepared by removing nucleus pulposus material and optionally decorticating the endplates. The clinician may then distract the vertebrae to expand the disc space to a desired height. Based on the distraction height, the clinician may then select a suitably dimensioned implant. The implant is then placed between two prongs located on the distal end of an implant inserter of the present invention. The prongs are then compressed by rotating a locking sleeve via a grip to securely engage the implant.

The clinician may insert the implant into the disc space by passing the inserter through the operative corridor of the access system (e.g. minimal access retractor). The clinician may take several fluoroscopic pictures to determine the location of the implant within the disc space by observing the location of the distal end of the inserter, and in particular the set of prongs. According to one embodiment of the present invention, the distal end of the implant inserter may be angled to facilitate insertion of the implant into disc space. Alternatively, the implant inserter may be generally straight and used to insert the implant into disc space before being rotating the implant 90-degrees to engage the endplates. Upon placement of the implant in the desired location within the disc space, the clinician may release the implant by rotating the sleeve via the grip counter-clockwise to decompress the set of prongs. A straight tamp may be used to guide the implant to the desired position. A footed tamp may be used to insert and compress autograft or other fusion-promoting composition (such as bone morphogenic protein) in the disc space. The clinician may then remove any distraction devices prior to the removal of the inserter so the vertebral endplates of the vertebrae engage with teeth provided on the top and bottom of the implant. Thereafter, the inserter may be withdrawn, the annulotomy closed, the access system removed, and the incision closed.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 14 is an exploded view of an exemplary 11 mm wide straight implant insertion tool according to one embodiment of the present invention, illustrating in particular the fork and collar components;

FIG. 15A is a top view of a fully assembled exemplary 11 mm wide straight implant insertion tool according to one embodiment of the present invention;

FIG. 15B is a side view diagram of an exemplary 11 mm wide straight implant insertion tool in accordance with one embodiment of the present invention;

FIG. 16E is a detailed side view diagram of an exemplary 11 mm wide implant insertion tool fork proximal end in accordance with one embodiment of the present invention;

FIG. 16F is a detailed end view diagram of an exemplary 11 mm wide implant insertion tool fork distal end in accordance with one embodiment of the present invention;

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The system and methods for performing transforaminal lumbar interbody fusion (TLIF) disclosed herein boasts a variety of inventive features and components that warrant patent protection, both individually and in combination.

The present invention may include a variety of devices for performing transforaminal lumbar interbody fusion, including but not limited to a variety of TLIF implants, implant inserters for inserting the TLIF implants into the intervertebral space, positioning devices for positioning the TLIF implants after insertion, and packing devices for packing additional materials within the disc space to promote fusion. Optional preparation devices may also be provided for preparing the intervertebral space prior to implant insertion. These devices will be described in detail below.

Figure 1:
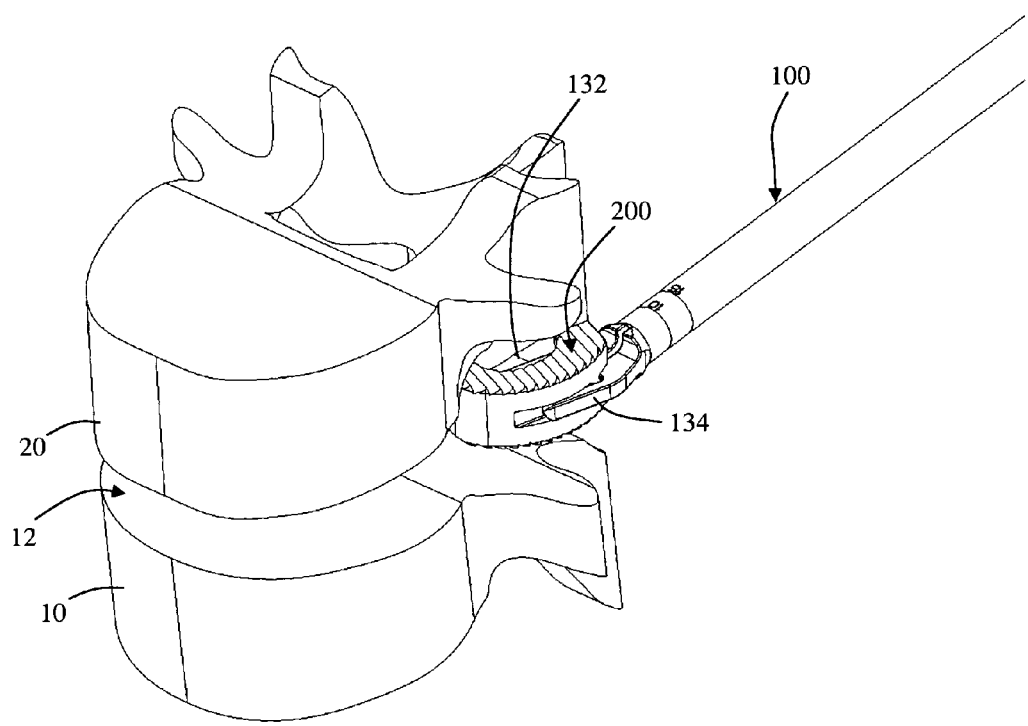
FIGS. 1-3 are perspective cut-away views of an exemplary process of inserting an exemplary implant using an exemplary inserter in accordance with the present invention.
Figure 2:
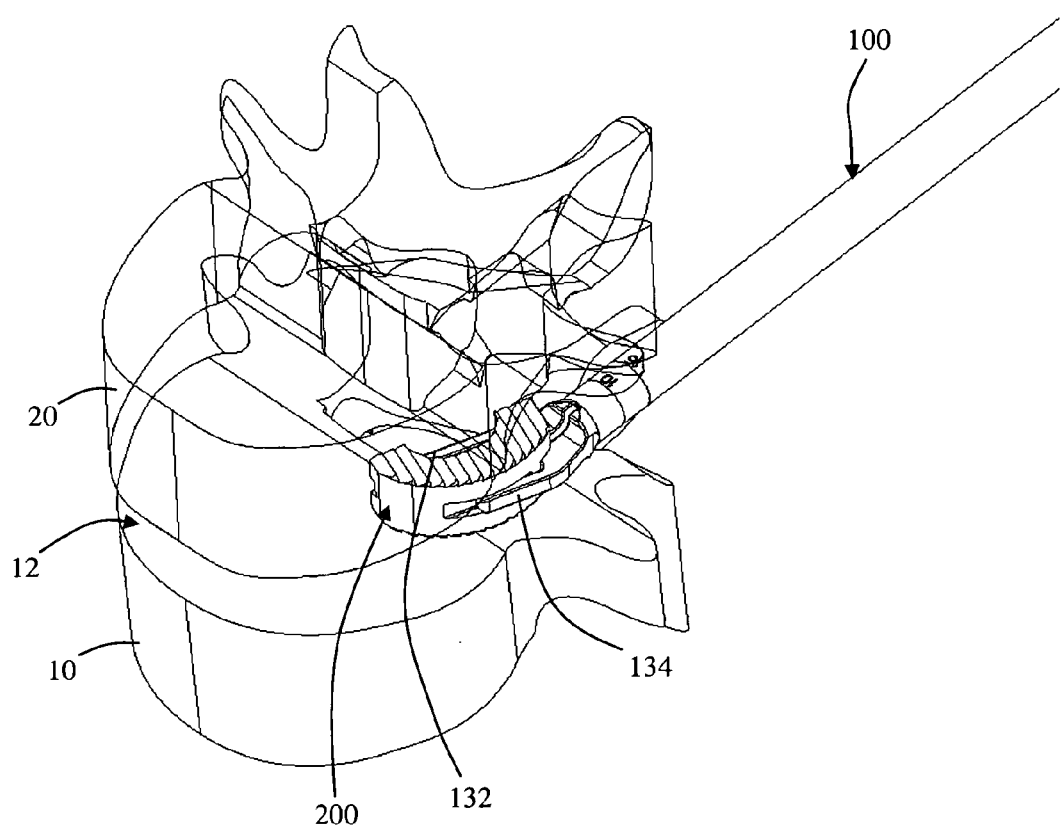
Figure 3:
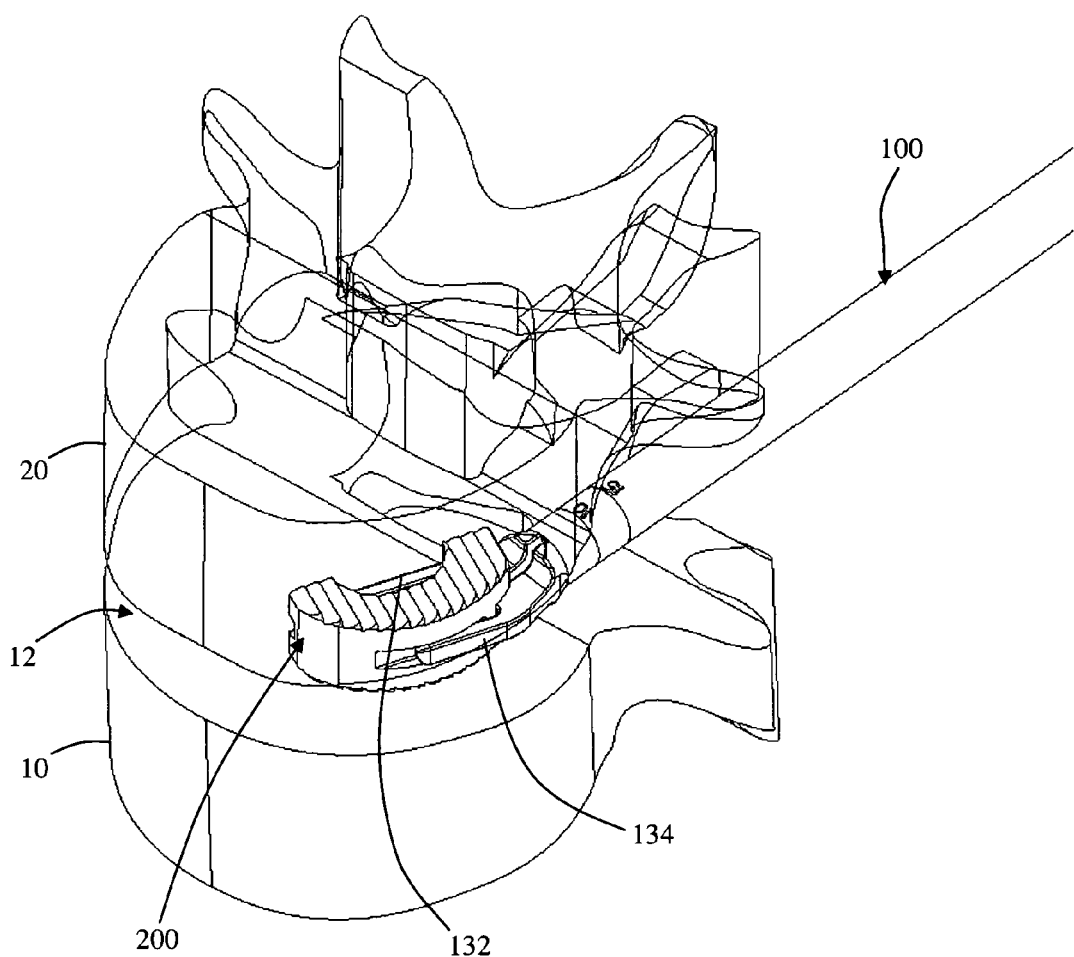

FIGS. 1-3 depict a cut-away view of an exemplary process of inserting an exemplary implant 200 using an exemplary inserter 100 in accordance with the present invention. In this process an exemplary implant 200 (shown in sectional view) is inserted via an inserter 100 into the disc space 12 of vertebrae 10, 20. Upper vertebra 20 is shown in wire line view to more clearly show the advancement of the implant 200 and inserter from FIG. 1 to FIG. 3 into the disc space 12. As shown, the inserter 100 grips the implant 200 via a set of prongs 132, 134. Ideally the prongs 132, 134 are fluoroscopically opaque. Accordingly, as the implant 200 is advanced from a position outside the disc space 12 (as shown in FIG. 1) to a desired position within the disc space 12 (as shown in FIG. 3), fluoroscopic images of the vertebrae 10, 20 would enable a clinician to determine the implant location in the disc space 12 by observing the position of the prongs 132, 134. Accordingly, the inserter 100 and method of the present invention may be used to accurately place an implant 200 within a disc space 12 regardless of the fluoroscopic properties of the implant (fluoroscopically opaque or transparent).

Figure 4A:
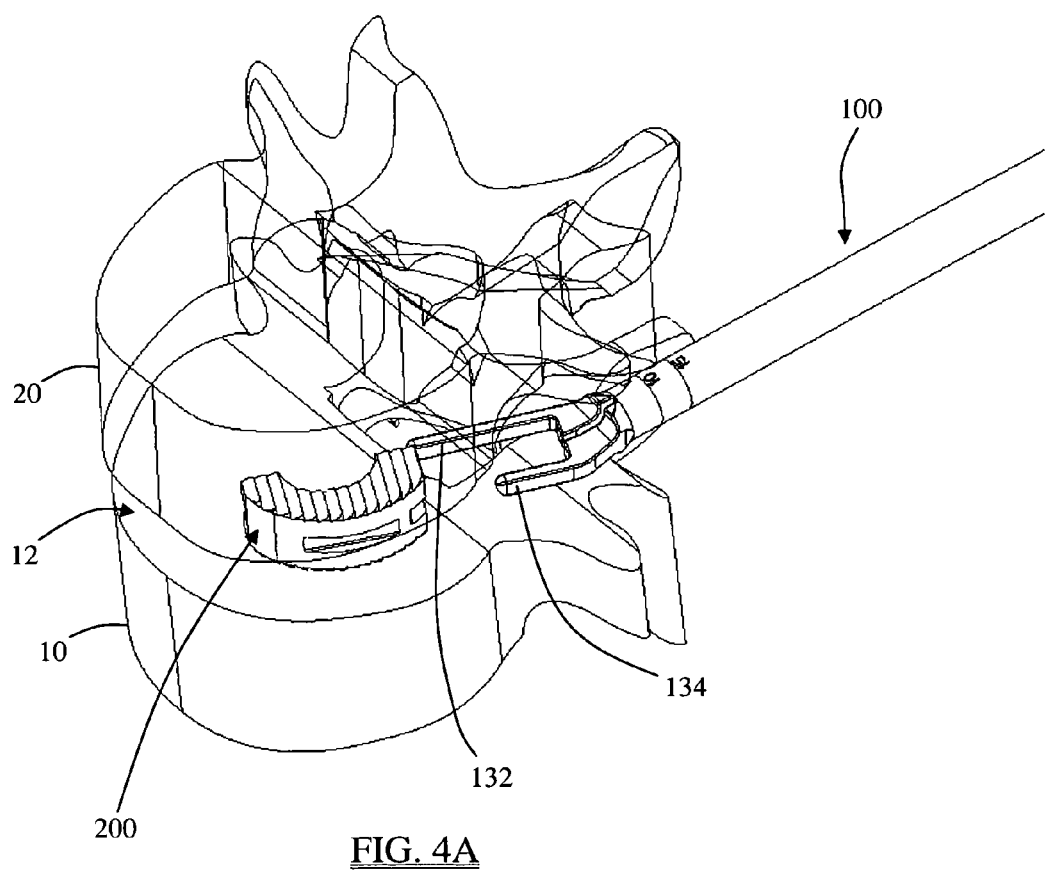
FIGS. 4A and 4B are perspective and top views, respectively, of an exemplary implant and inserter according to one embodiment of the present invention illustrating the positioning of the implant just after release from the inserter.
Figure 4B:
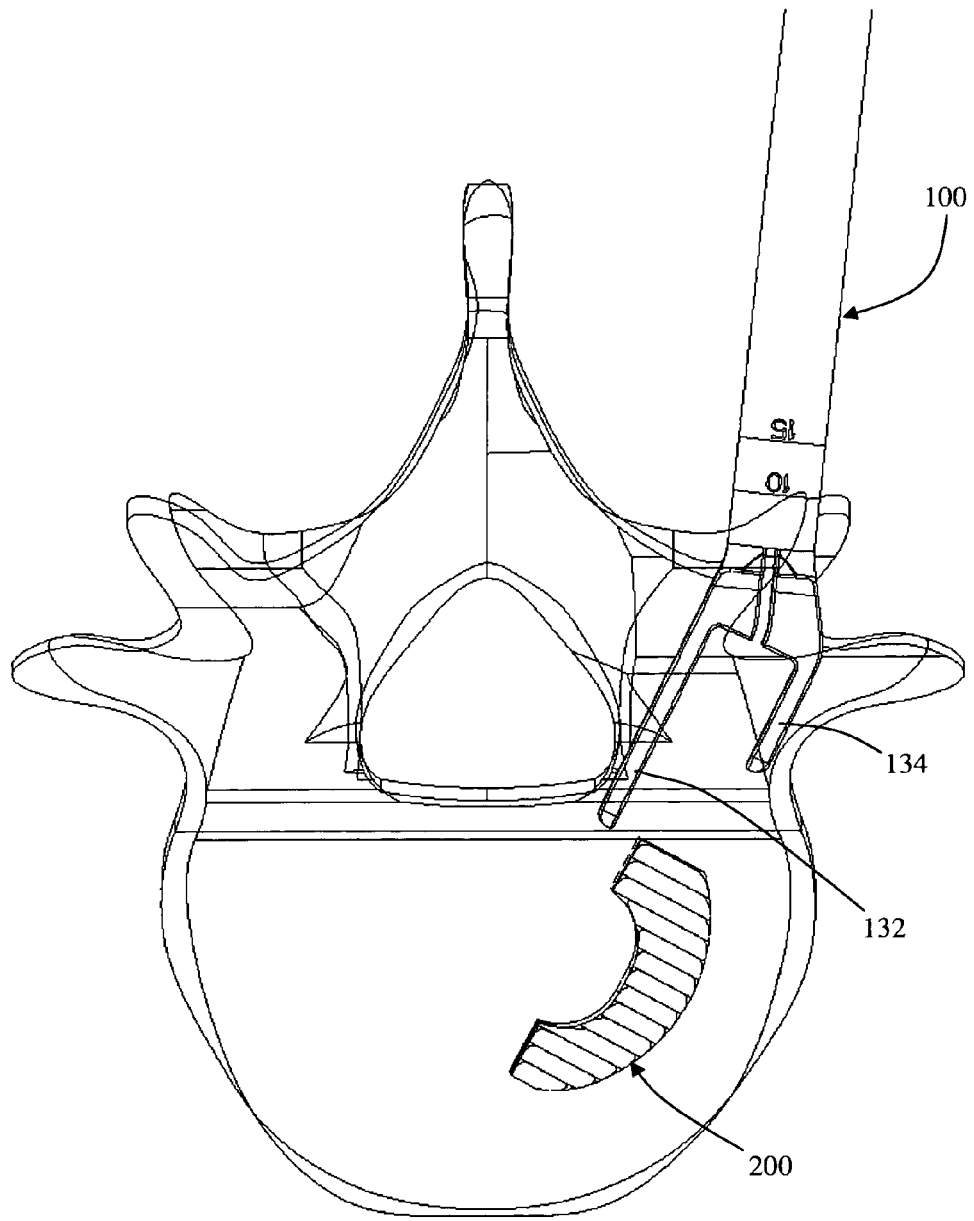
Figure 5A:
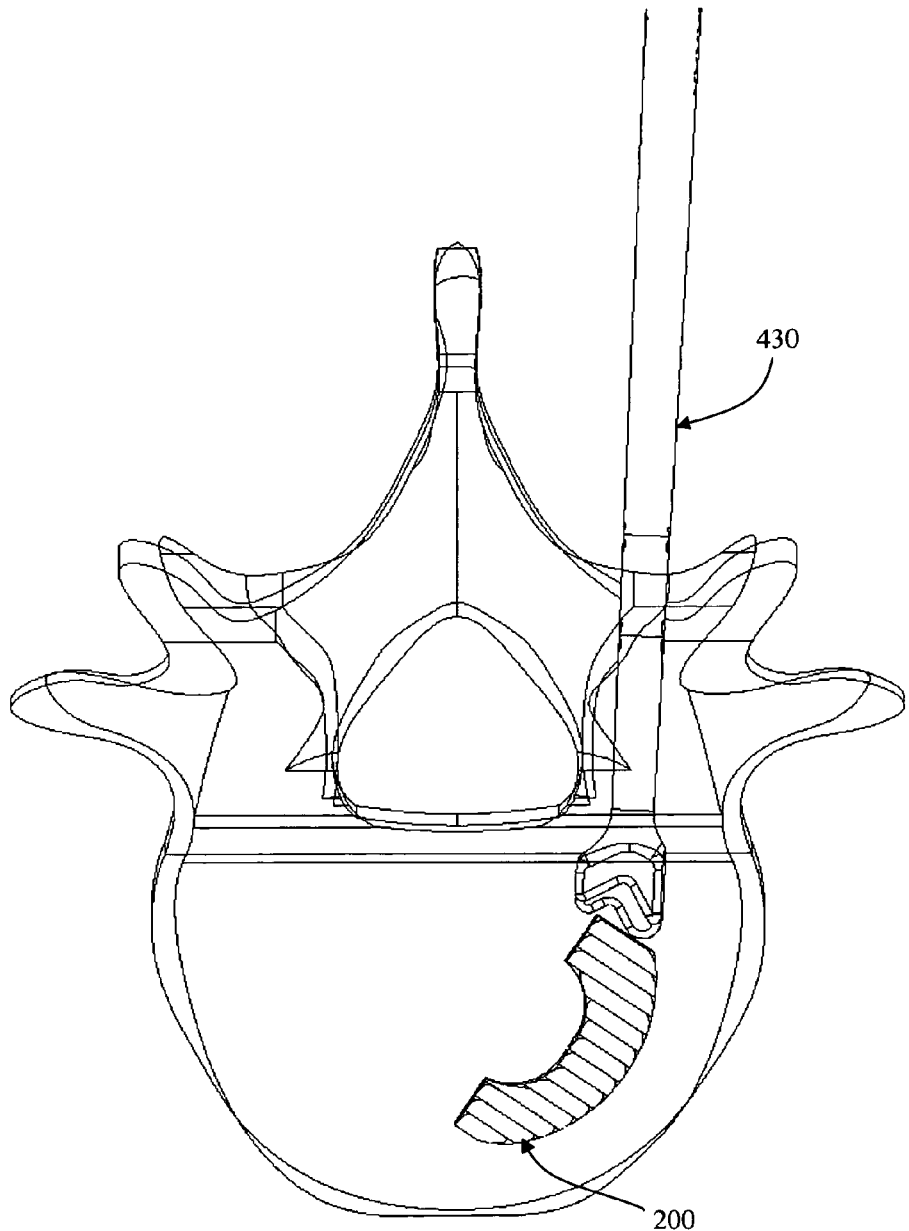
FIGS. 5A and 5B are top views of an exemplary implant and straight tamp in use according to one embodiment of the present invention.
Figure 5B:
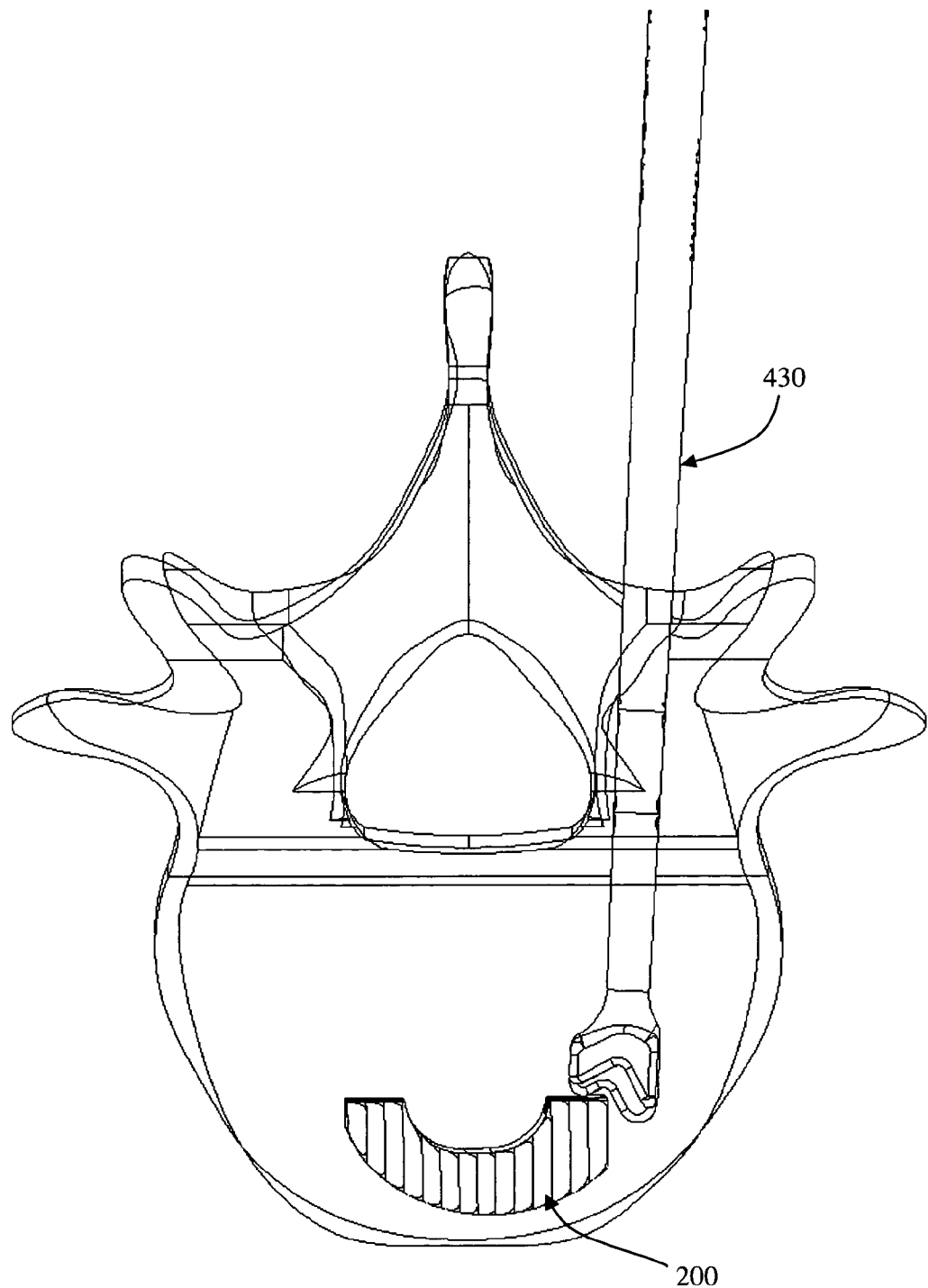
Figure 5C:
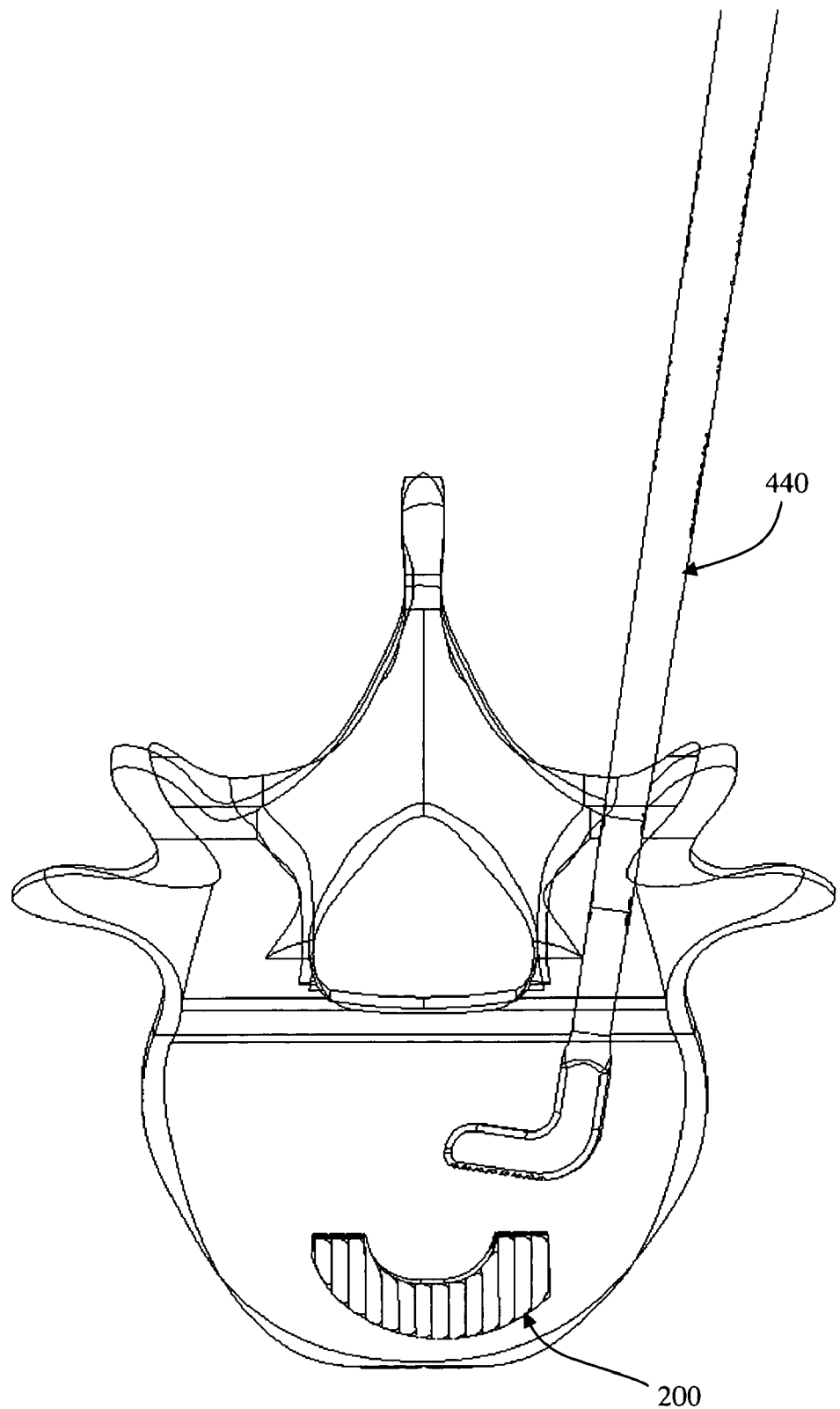
FIG. 5C is a top view of an exemplary implant and footed tamp according to one embodiment of the present invention.

FIGS. 4A-6D illustrate an exemplary process of positioning implant 200 into a desired location according to one embodiment of the present invention. As shown in FIGS. 4A & 4B, after the implant 200 is inserted into the disc space 12, the implant 200 is released from the inserter 100 as described in further detail below. As shown in FIGS. 5A & 5B, a straight tamp 420 may be used to guide implant 200 to a desired position. Once implant 200 is in its desired position, a clinician may add and pack in autograft or other fusion-assisting composition (such as bone morphogenic protein) using a footed tamp 430, as shown in FIG. 5C.

Figure 6A:
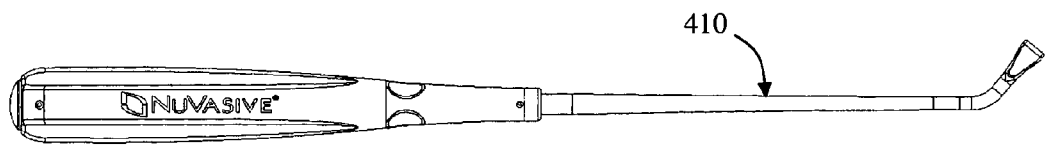
FIG. 6A is a top view of an exemplary scraper according to one embodiment of the present invention.
Figure 6B:
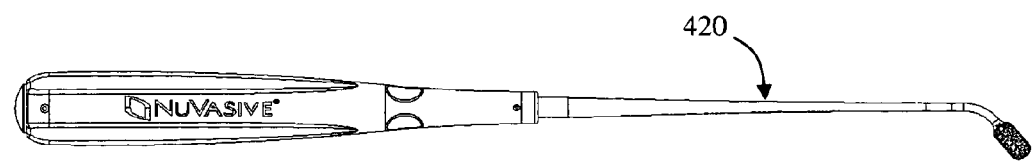
FIG. 6B is a top view of an exemplary rasp according to one embodiment of the present invention.
Figure 6C:
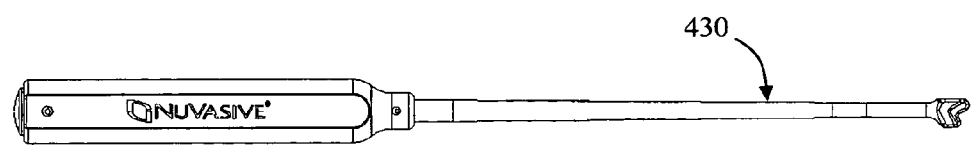
FIG. 6C is a top view of an exemplary straight tamp according to one embodiment of the present invention.
Figure 6D:
FIG. 6D is a top view of an exemplary footed tamp according to one embodiment of the present invention.

FIGS. 6A-6D illustrate a variety of instruments that may be used according to the present invention. FIG. 6A depicts a scraper 410 that may be used to clean out a disc space 12 prior to insertion of implant 200. FIG. 6B is a line drawing of an exemplary rasp 420 according to the present invention, used to further clean out the disc space 12 prior to insertion of implant 200. FIG. 6C is a line drawing of an exemplary straight tamp 430 according to one embodiment of the present invention, used to guide implant 200 into position after insertion into disc space 12. FIG. 6D is a line drawing of a footed tamp 440 according to the present invention, that may be used to insert and compress allograft material into the disc space 12 once implant 200 has been inserted and positioned.

The implant 200 of the present invention may be provided in any number of suitable shapes and sizes. In a preferred embodiment, however, the implant 200 may comprise the exemplary shapes and size ranges as shown and detailed in FIGS. 7A-10D. The exemplary implant 200 may have a width of 9 or 11 millimeters and a length of 20 or 25 millimeters. Further, as shown in Size Tables 1-4, the exemplary implant 200 may have a height from 6 to 16 millimeters in 2 mm increments in one exemplary embodiment. The basic geometry of exemplary implant 200 is similar for each of these size variations. The implant 200 is crescent shaped with a top 210, bottom 220, proximal end 230, distal end 260, left side 240, and right side 250. The top 210 and bottom 220 include a plurality of rows of teeth 212 where the teeth are designed to engage vertebra endplates upon insertion between vertebrae. The implant sides 230, 240, 250, 260 may include a plurality of tool engaging recesses 232, 234, 236, and 242. The left side 240 of implant 200 is curved while the tool recess 242 is straight. The right side 250 has a curved section 252 and flat sections corresponding to the tool engaging recesses 234, 236. The proximal end 230 of implant 200 has a flat end and the tool engaging recess 232 also has a flat end with a pair of 45-degree offsets that mate with the tool recesses 234, 242.

Figures 7A, 7B:
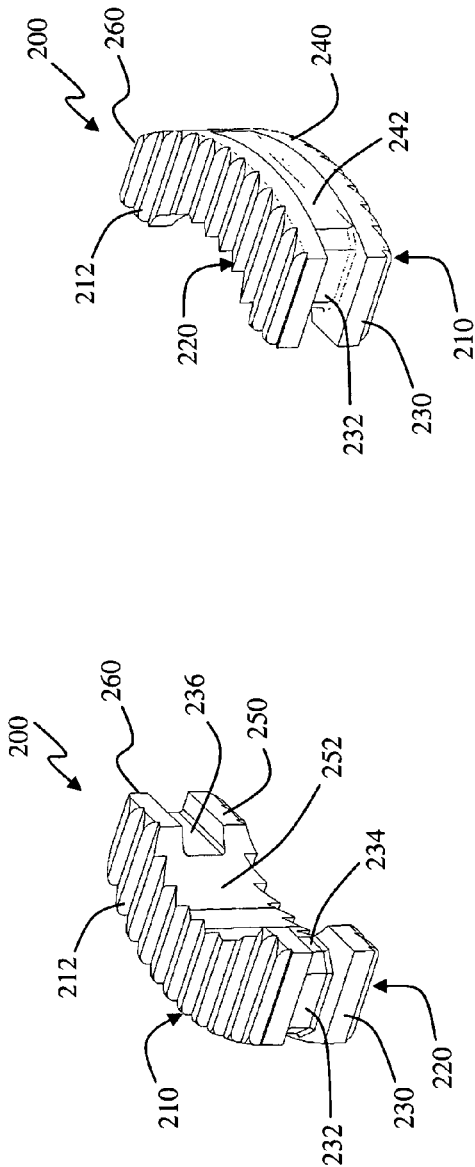
FIG. 7A is a perspective right side isometric view of an exemplary implant according to one embodiment of the present invention having the dimensions of 8 mm tall, 9 mm wide, and 20 mm long.
FIG. 7B is a perspective left side isometric view of the exemplary implant of FIG. 7A.
Figure 7C:
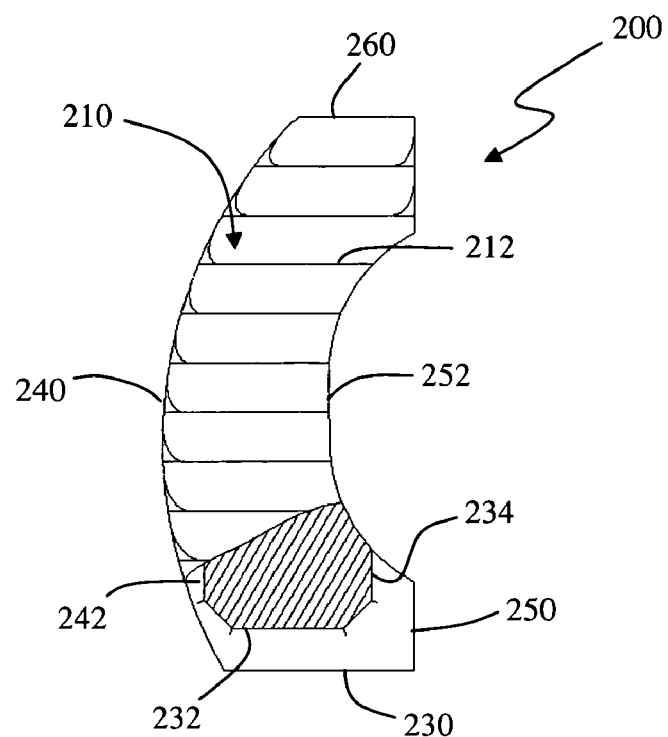
FIG. 7C is a top view of the exemplary implant of FIG. 7A.
Figure 7D:
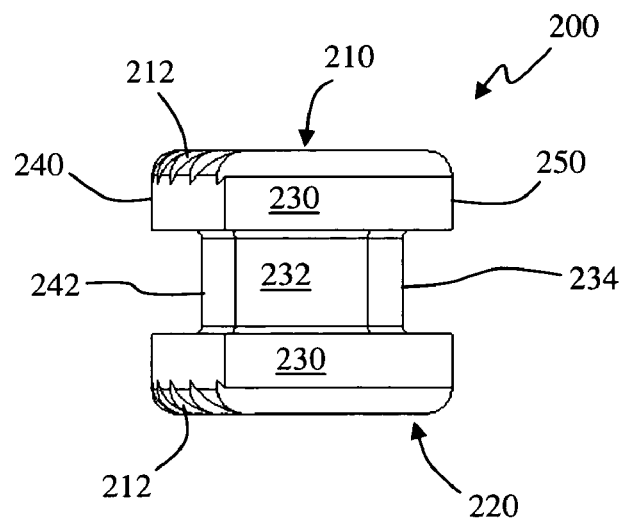
FIG. 7D is a tool base engaging side view of the exemplary implant of FIG. 7A.
Figure 7E:
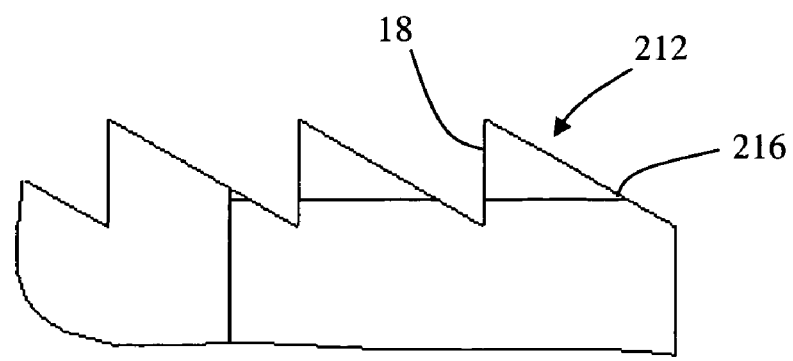
FIG. 7E is an exploded view of a plurality of teeth located on the exemplary implant of FIG. 7A.
Figure 7F:
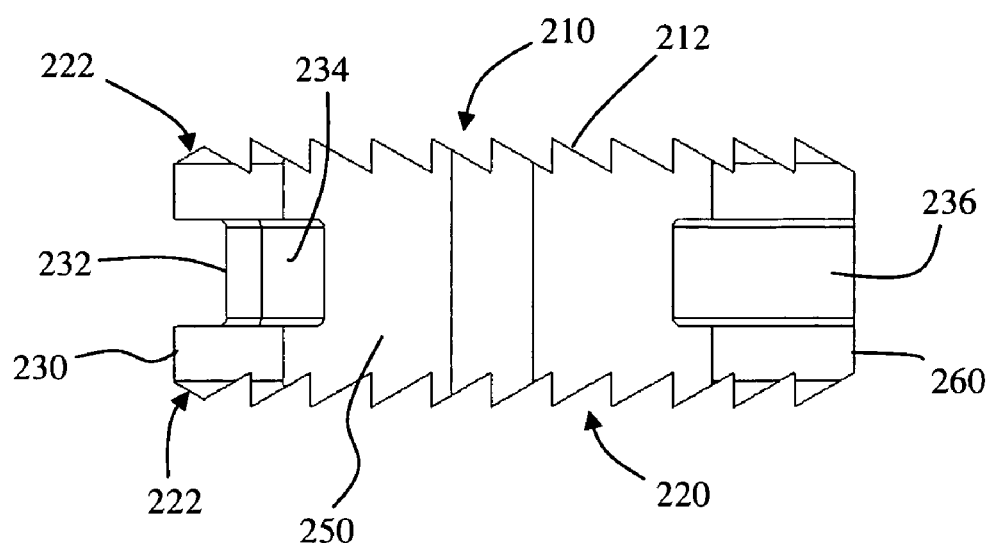
FIG. 7F is a right side view of the exemplary implant of FIG. 7A.

In further detail, FIG. 7A is a top, right side perspective view isometric line drawing of an exemplary implant 200 having dimensions of 8 mm tall, 9 mm wide, and 20 mm long. FIG. 7B is a bottom, left side perspective view isometric line drawing of the exemplary implant 200 of FIG. 7A. FIGS. 7C and 7D are top view and proximal end view line drawings, respectively, of the exemplary 8 mm tall, 9 mm wide, 20 mm long implant 200. FIG. 7E is a detailed view line drawing of several teeth 212 for an exemplary 8 mm tall, 20 mm long implant 200. As shown, each tooth has a top 216 and side 218 wherein the top has a 60-degree inclination relative to the flat surface of the implant top 210 or bottom 220. As indicated, the exemplary 20 mm long implant 200 has 22 such teeth 212. FIG. 7F is a right side view line drawing of the implant 200 of FIG. 7A illustrating the general shape of two 45-degree teeth 222 disposed on the proximal end 230.

Figures 8A, 8B:
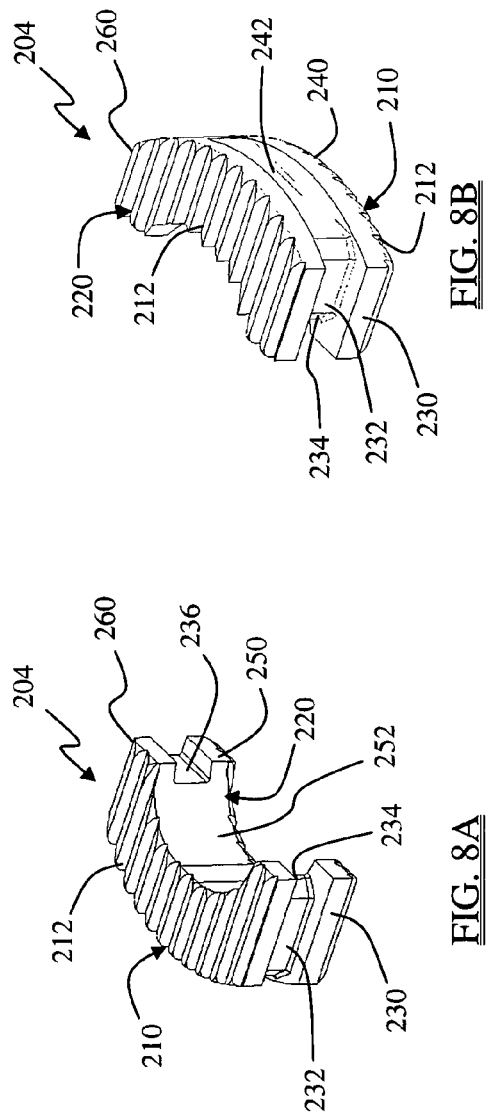
FIGS. 8A and 8B are perspective right and left side isometric views, respectively, of an exemplary implant according to one embodiment of the present invention having the dimensions of 8 mm tall, 11 mm wide, and 20 mm long.
Figure 8C:
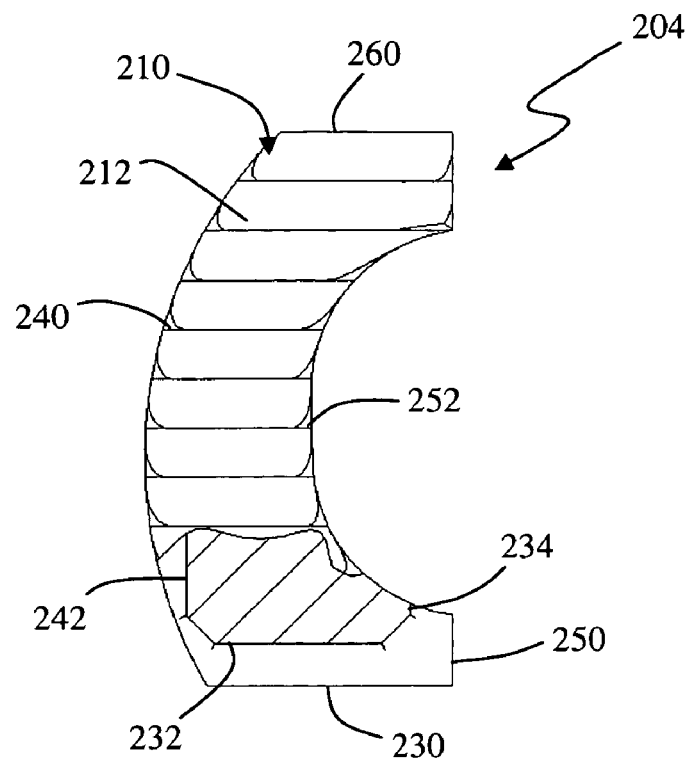
FIG. 8C is a top view of the exemplary implant of FIG. 8A.
Figure 8D:
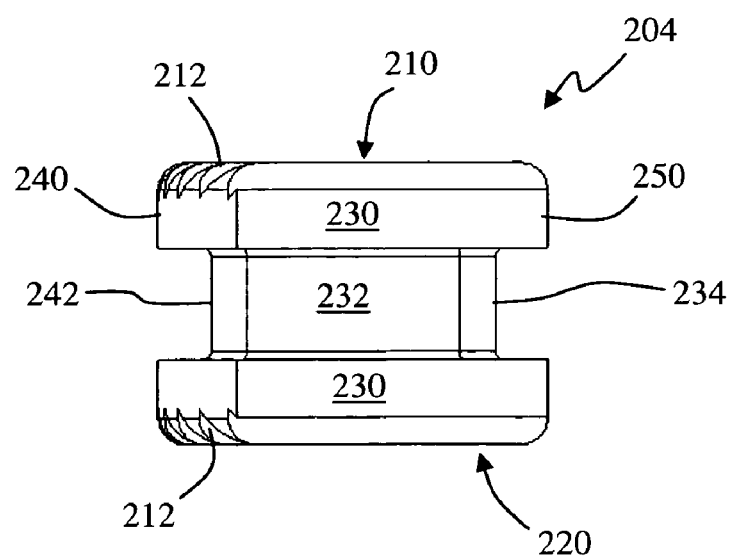
FIG. 8D is a tool base engaging side view of the exemplary implant of FIG. 8A.

FIG. 8A is a top, right side isometric line drawing of an exemplary implant 204 having dimensions of 8 mm tall, 11 mm wide, and 20 mm long. FIG. 8B is a bottom, left side isometric line drawing of the exemplary 8 mm tall, 11 mm wide, 20 mm long implant 204. FIG. 8C is a top view line drawing of the exemplary 8 mm tall, 11 mm wide, 20 mm long implant 204. FIG. 8D is a proximal end view line drawing of the exemplary 8 mm tall, 11 mm wide, 20 mm long implant 204.

Figures 9A, 9B:
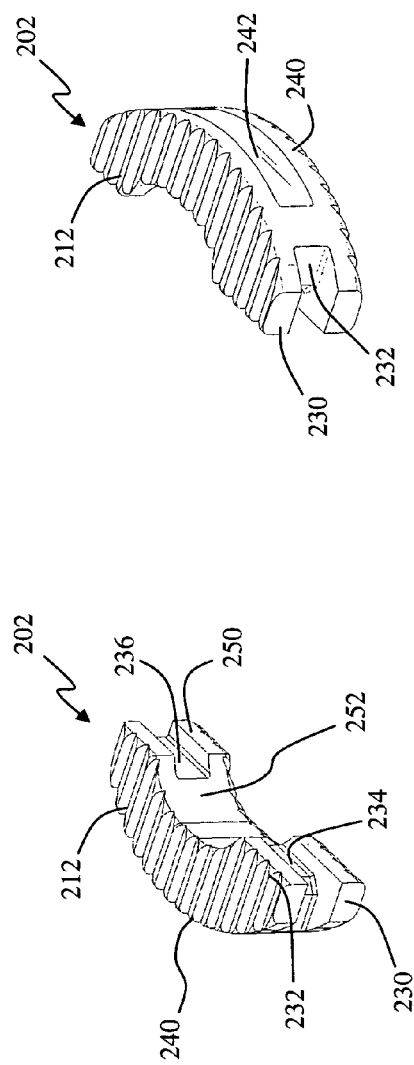
FIGS. 9A and 9B are perspective right and left side isometric views, respectively, of an exemplary implant according to one embodiment of the present invention having the dimensions of 8 mm tall, 9 mm wide, and 25 mm long.
Figure 9C:
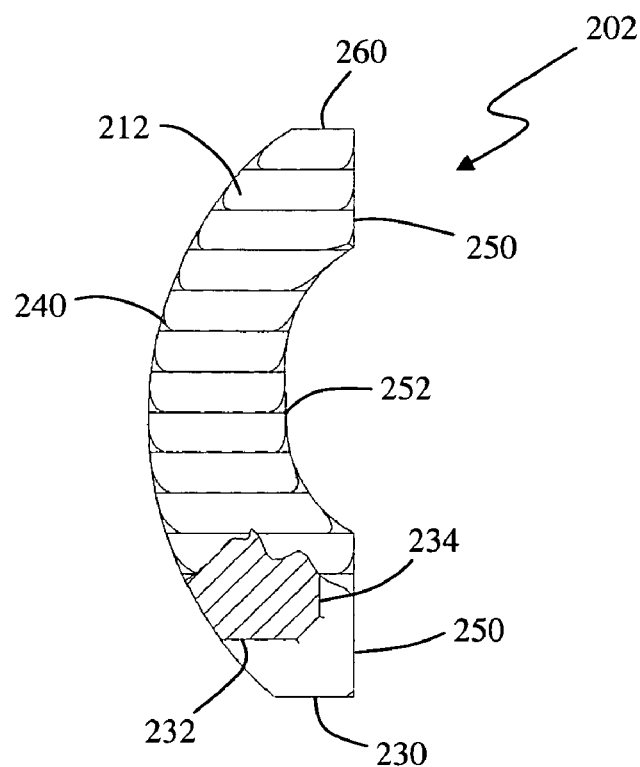
FIG. 9C is a top view of the exemplary implant of FIG. 9A.
Figure 9D:
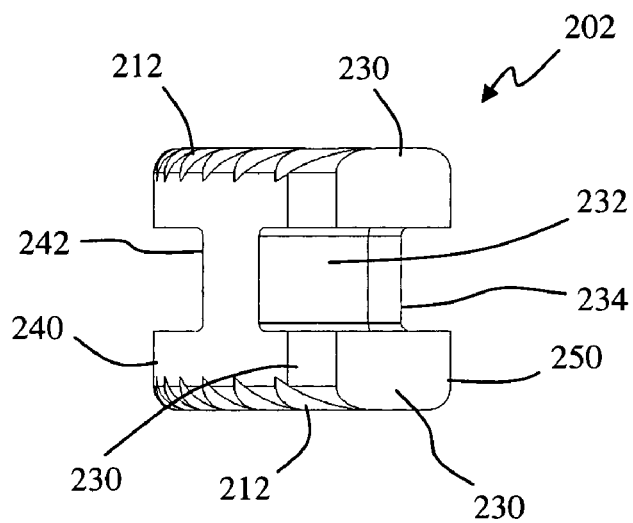
FIG. 9D is a tool base engaging side view of the exemplary implant of FIG. 9A.
Figure 9E:
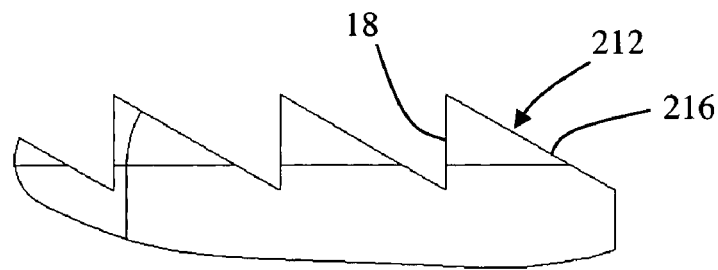
FIG. 9E is an exploded view of a plurality of teeth located on the exemplary implant of FIG. 9A.
Figure 9F:
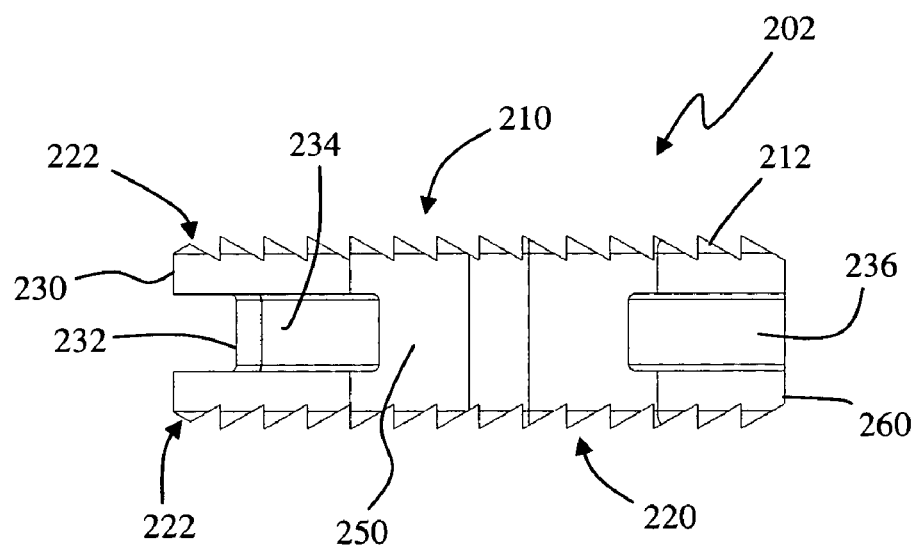
FIG. 9F is a right side view of the exemplary implant of FIG. 9A.

In further detail, FIG. 9A is a top, right side isometric line drawing of an exemplary implant 202 having dimensions of 8 mm tall, 9 mm wide, and 25 mm long. FIG. 9B is a bottom, left side isometric line drawing of the exemplary 8 mm tall, 9 mm wide, 25 mm long implant 202. FIG. 9C is a top view line drawing of the exemplary 8 mm tall, 9 mm wide, 25 mm long implant 202. FIG. 9D is a proximal end view line drawing of the exemplary 8 mm tall, 9 mm wide, 25 mm long implant 202. FIG. 9E is a detailed view line drawing of several teeth 212 for an exemplary 25 mm long implant 202. As shown, each tooth has a top 216 and side 218 where the top has a 60-degree inclination relative to the flat surface of the implant top 210 or bottom 220. As indicated, the exemplary 25 mm long implant 200 has 28 such teeth 212. FIG. 9F is a right side view line drawing of an exemplary 8 mm tall, 25 mm long implant 202 that indicates the dimensions of the two 45-degree teeth 222.

Figure 10B:
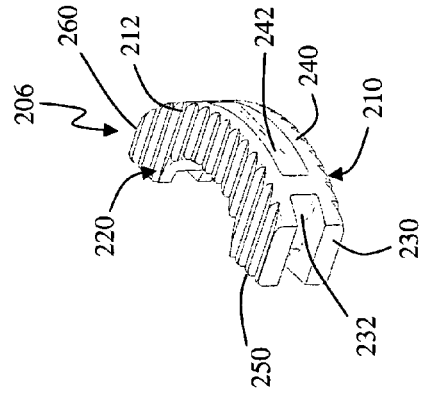
FIGS. 10A and 10B are perspective right and left side isometric views, respectively, of an exemplary implant according to one embodiment of the present invention having the dimensions of 8 mm tall, 11 mm wide, and 25 mm long.
Figure 10A:
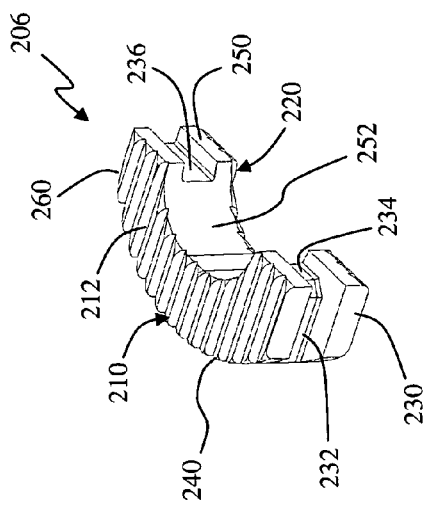
Figure 10C:
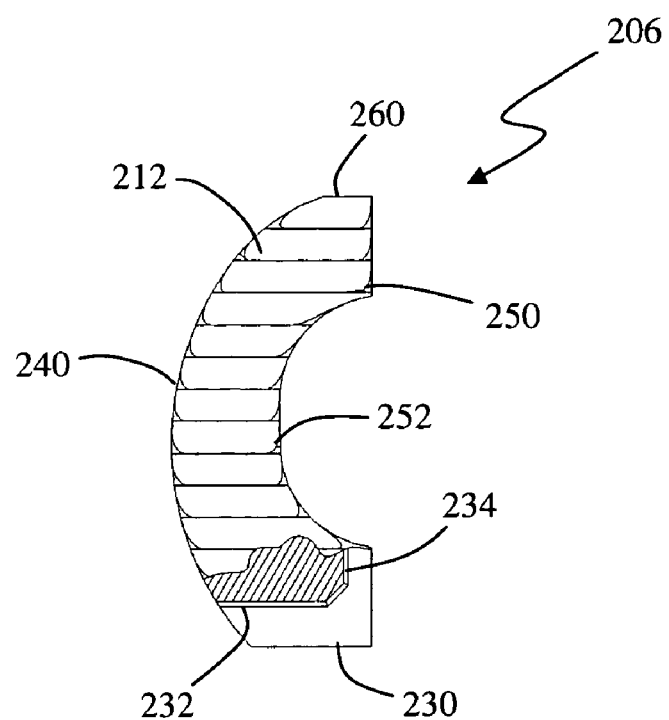
FIG. 10C is a top isometric view of the exemplary implant of FIG. 10A.
Figure 10D:
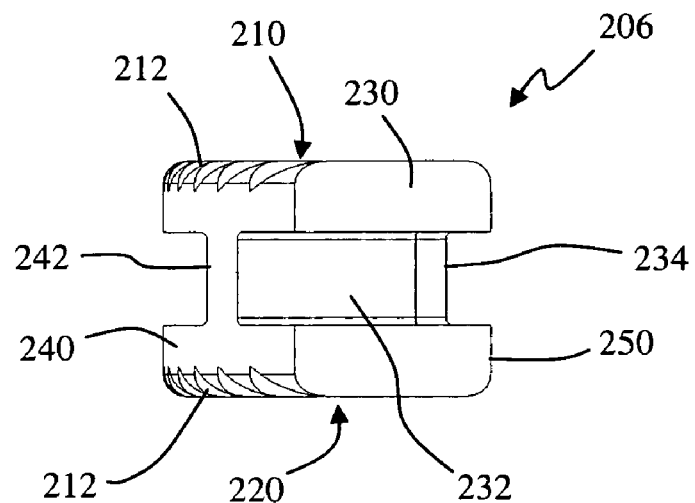
FIG. 10D is a tool base engaging side view of the exemplary implant of FIG. 10A.

FIG. 10A is a top, right side isometric line drawing of an exemplary implant 206 having dimensions of 8 mm tall, 11 mm wide, and 25 mm long. FIG. 10B is a bottom, left side isometric line drawing of the exemplary 8 mm tall, 11 mm wide, 25 mm long implant 206. FIG. 10C is a top view line drawing of the exemplary 8 mm tall, 11 mm wide, 25 mm long implant 206. FIG. 10D is a proximal end view line drawing of the exemplary 8 mm tall, 11 mm wide, 25 mm long implant 206 of FIGS. 10A-10C.

Figure 11:
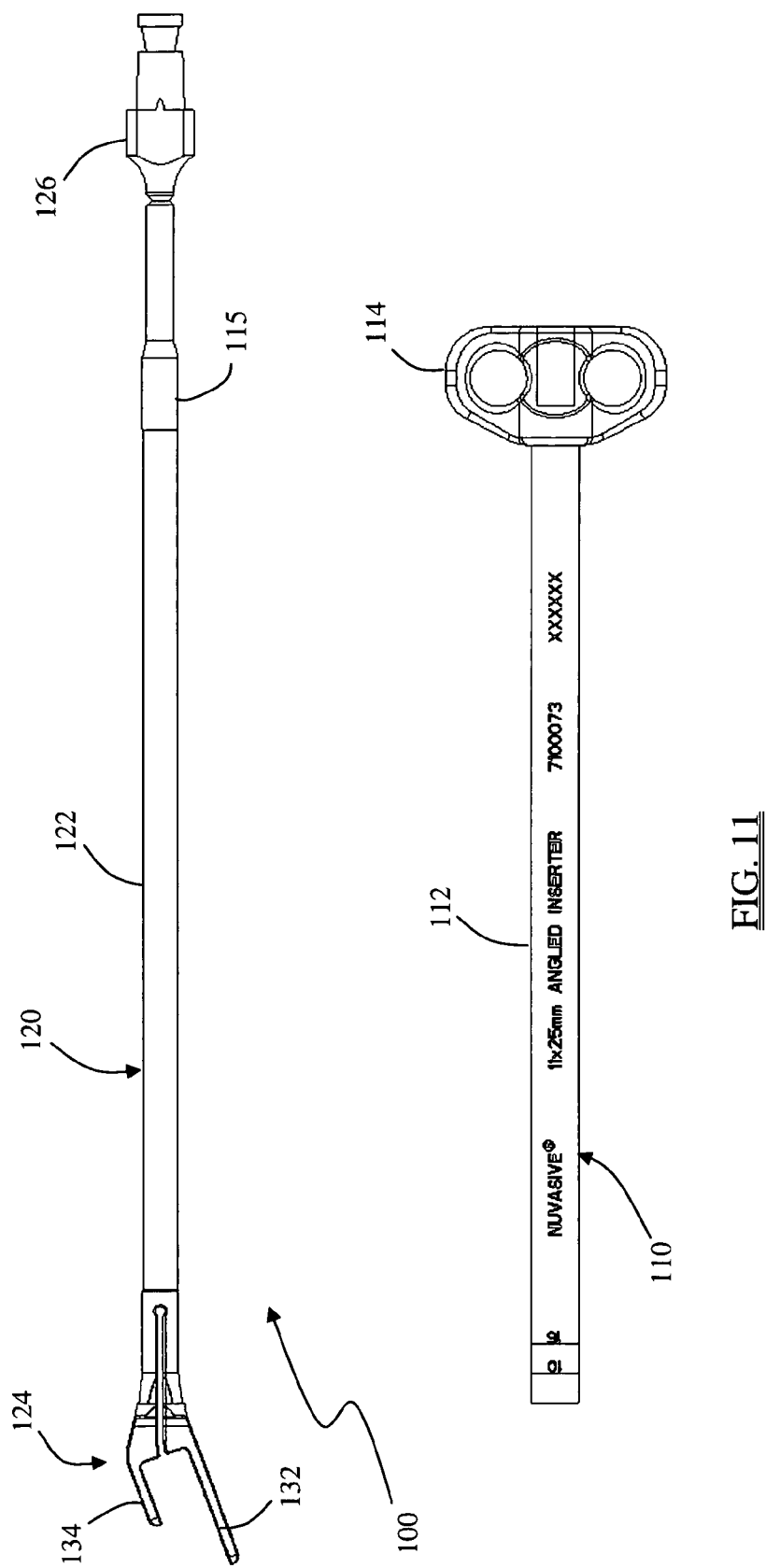
FIG. 11 is an exploded view of an exemplary 11 mm wide angled inserter according to one embodiment of the present invention, illustrating in particular the fork and collar components.

FIGS. 11-16F are views of different configurations of the exemplary inserter 100 in accordance with the present invention. FIG. 11 is an isometric line drawing of the 11 mm wide angled implant inserter 100 in its two parts: the collar 110 and fork 120. The fork 120 includes a shaft 122, a proximal tool-engaging end 126 and a distal implant gripping end 124. The proximal tool-engaging end 126 includes a set of external threads 115. The distal implant gripping end 124 includes a set of prongs 132, 134 for interaction with the implant 200. The collar 110 includes a hollow sleeve 112 dimensioned to slide over the proximal end 126 of the fork 120 and engage the distal end 124. The collar 110 includes a grip 114 with internal receiving threads 128 therein where the internal receiving threads 128 engage the external threads 115 of fork 120 when the sleeve 112 is slid over the proximal end 126 of fork and 120 approaches the distal end 124. The grip 114 is rotated clockwise to further advance the distal end of collar 110. The distal end 124 of fork 120 is dimensioned so that the collar 110 will compress the set of prongs 132, 134 upon advancement of the distal end of collar 110 by clockwise rotation of the sleeve 112 via the grip 114. When an implant 200 is placed between the set of prongs 132, 134, the prongs 132, 134 may be advanced toward each other to securely engage the implant 200 upon clockwise rotation of the grip 114. The implant 200 may be similarly released from the prongs 132, 134 by rotating the sleeve 112 counterclockwise when desired, such as when the implant is positioned in a desired location between vertebrae 10 and 20 as shown in FIG. 4.

Figure 12A:
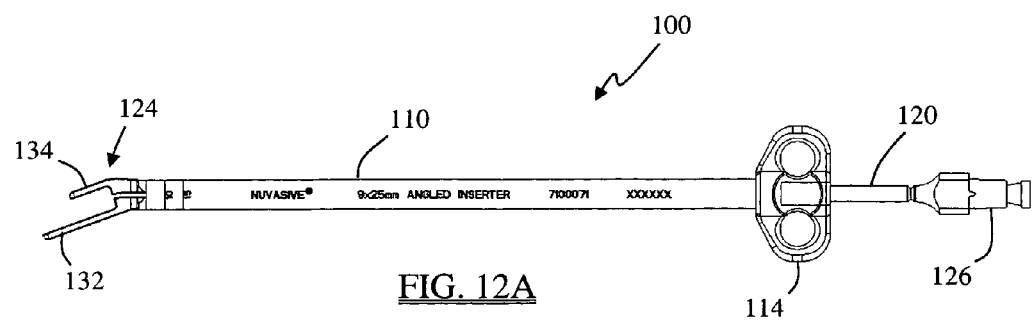
FIG. 12A is a top view of an exemplary 9 mm wide angled inserter according to one embodiment of the present invention.
Figure 12B:
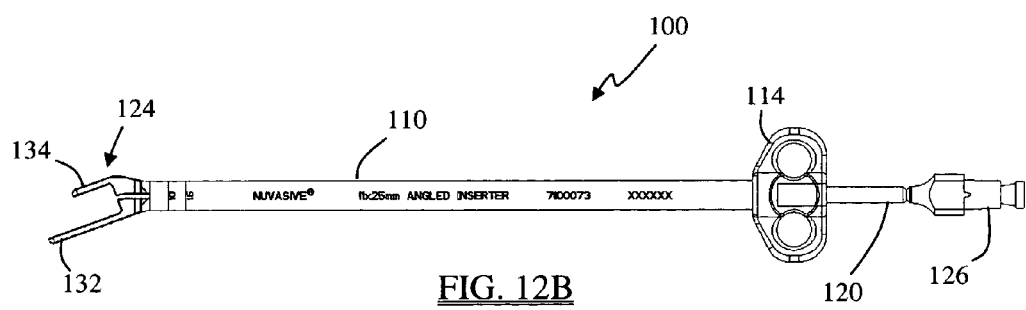
FIG. 12B is a top view of an exemplary 11 mm wide angled inserter according to one embodiment of the present invention.
Figure 12C:
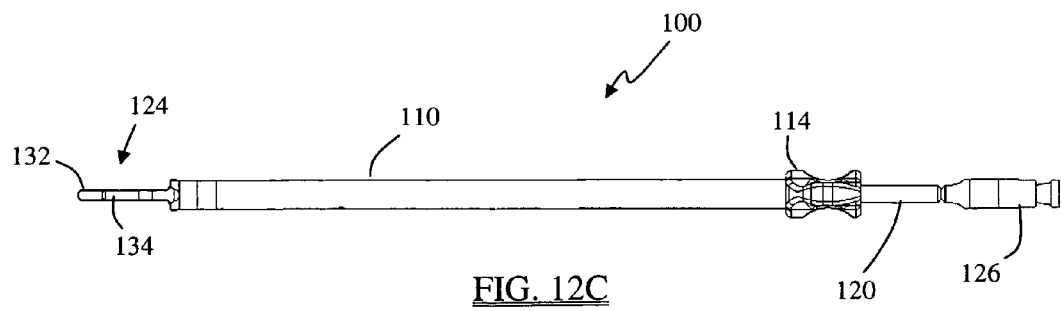
FIG. 12C is a side view of the exemplary 9 mm wide angled inserter of FIG. 12A.

FIGS. 12A & 12B are top views of line drawings of the 9 mm and 11 mm, respectively, of angled implant inserters 100, and FIG. 12C is a side view of the line drawing of the 9 mm wide angled implant inserter 100. By way of example only, the inserter 100 is shown with a length of about 10 inches from the distal end 124 to the grip 114. Alternatively, inserter 100 may be of any length desirable to insert the implant 200 into the desired location. This enables a clinician to use the inserter 100 to place an implant 200 between vertebrae in a minimally invasive procedure, such as via the use of a multi-blade retractor as described below.

Figure 13A:
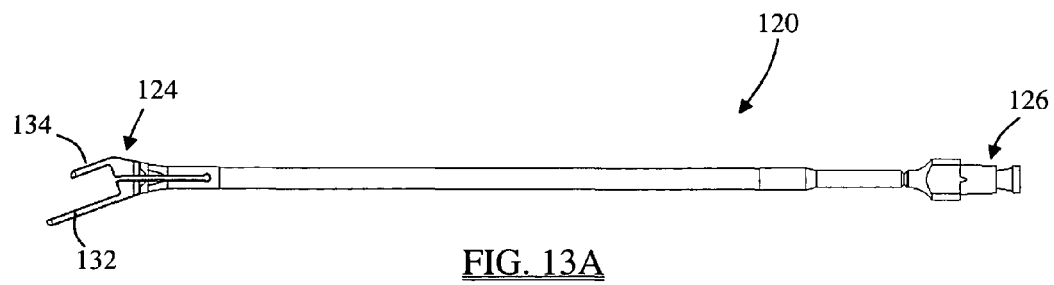
FIG. 13A is a top view of an exemplary fork component according to one embodiment of the present invention.
Figure 13B:
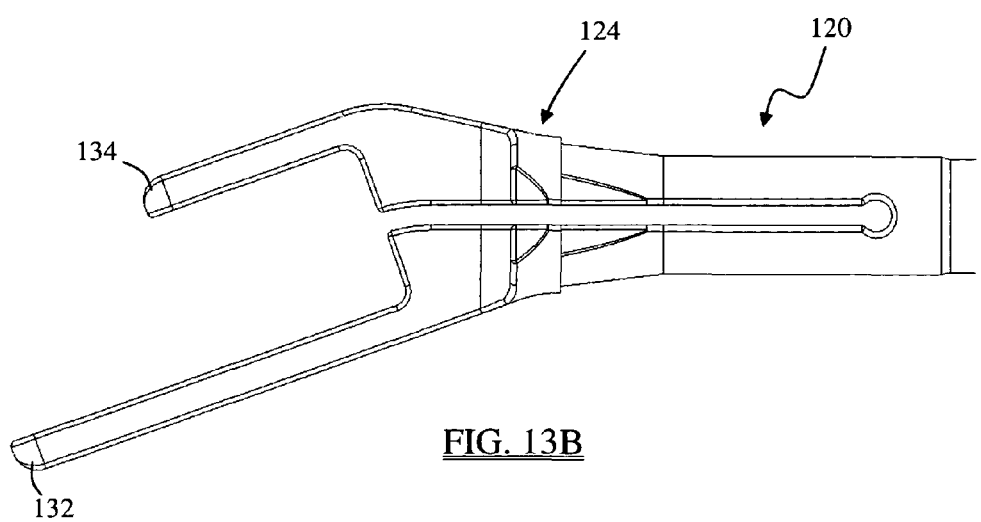
FIG. 13B is a side view of an exemplary angled implant insertion tool distal end according to one embodiment of the present invention.
Figure 13C:
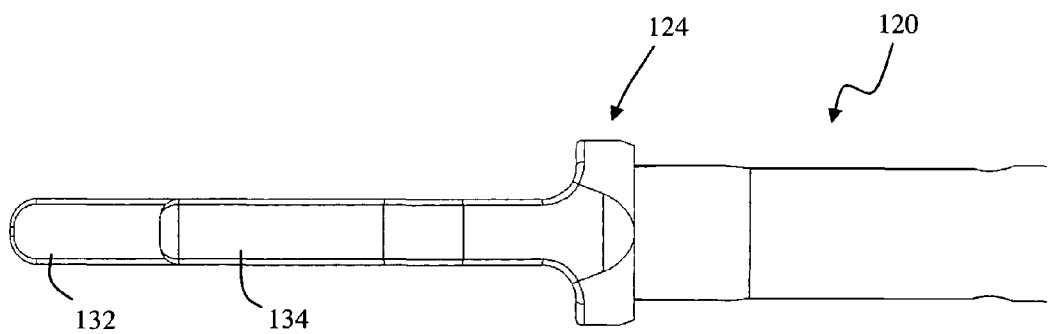
FIG. 13C is a top view of the angled implant insertion tool distal end of FIG. 13B.
Figure 13D:
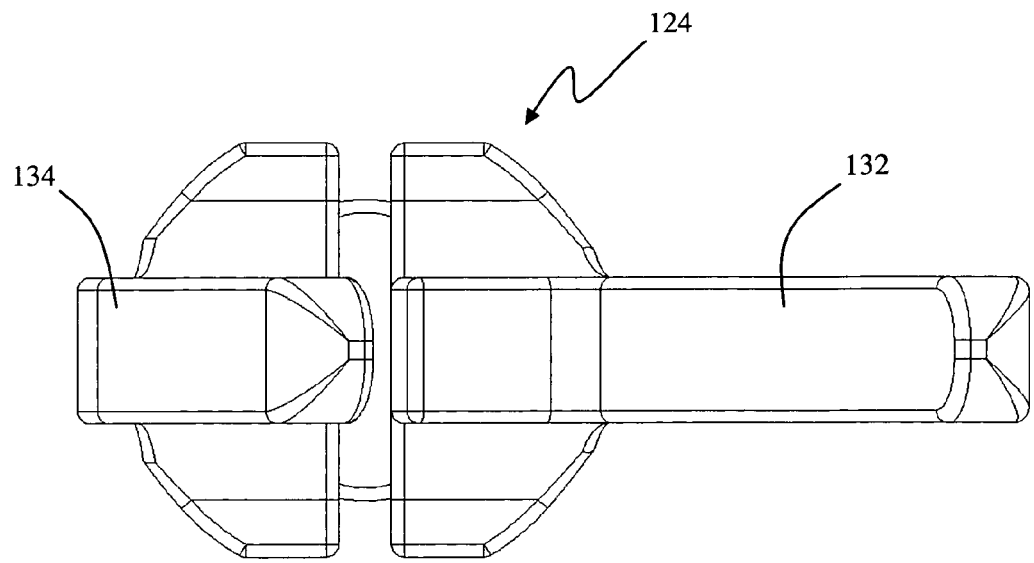
FIG. 13D is a front view of the angled implant insertion tool distal end of FIG. 13B.
Figure 13E:
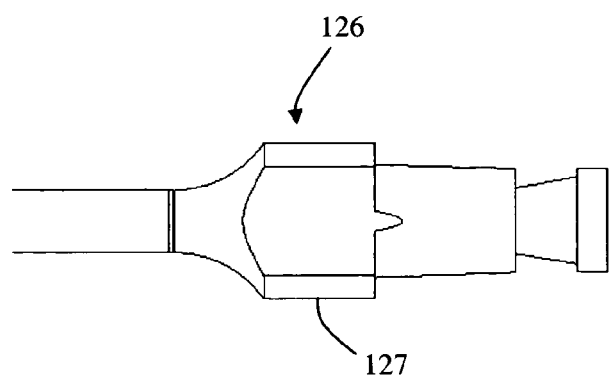
FIG. 13E is a side view of an exemplary implant insertion tool proximal end according to one embodiment of the present invention.

FIGS. 13A-13E are line drawings of the exemplary 11 mm wide implant fork 120. FIG. 13A is a top view line drawing of one embodiment of the fork 120, illustrating in particular the angled nature of prongs 132, 134. This angled relationship of prongs 132, 134 enables an implant 200 to be slightly angled with respect to vertebrae 10, 20 in turn allowing for a steeper (i.e. more vertical) angle of entry into the spinal column by the clinician. FIG. 13B is a top view line drawing of the distal end 124 of fork 120, FIG. 13C is a side view line drawing of the distal end 124 of fork 120, and FIG. 13D is an end view line drawing of the distal end 124 of fork 120. As shown, the distal end 124 includes a set of prongs 132, 134 and a compressible section 136. As shown, the first prong 132 may be compressed toward the second prong 134 up to a distance of about 0.40 inches. In an exemplary embodiment, when the distal end of collar 110 is advanced over the tapered end 137 of the compressible section 136 of fork 120, the prongs 132, 134 are compressed toward each other. FIG. 13E is a side view line drawing of the tool engaging proximal end 126 of fork 120. As shown, the tool engaging proximal end 126 includes a formation 127 to allow coupling to a handle (not shown).

Figure 16A:
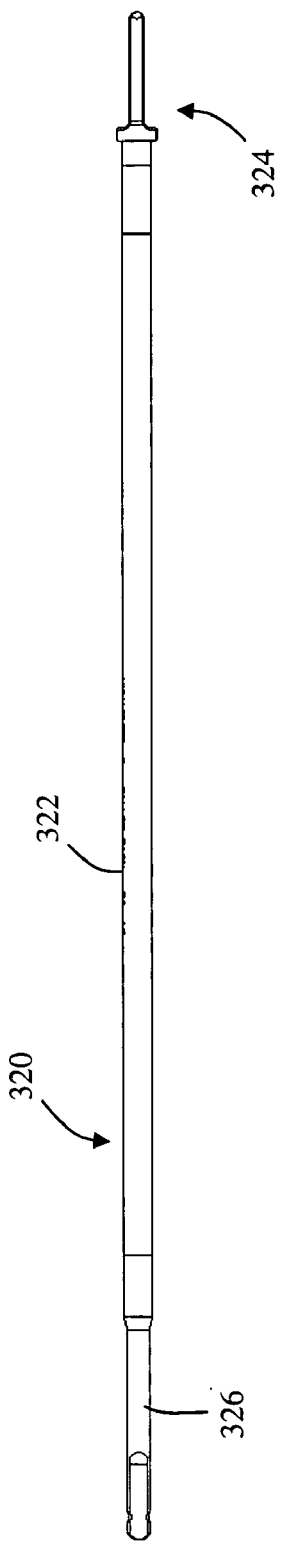
FIG. 16A is a side view diagram of an exemplary 11 mm wide straight implant insertion tool fork in accordance with one embodiment of the present invention.
Figure 16B:
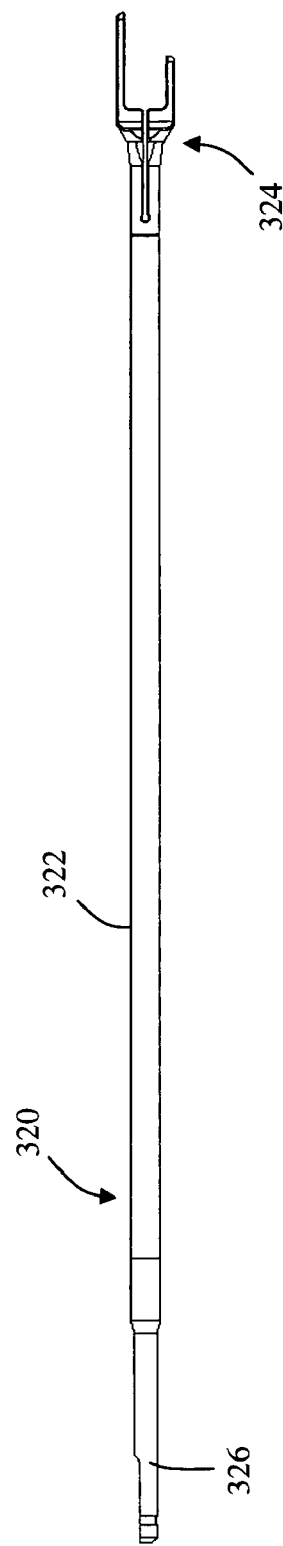
FIG. 16B is a top view diagram of an exemplary 11 mm wide straight implant insertion tool fork in accordance with one embodiment of the present invention.
Figure 16C:
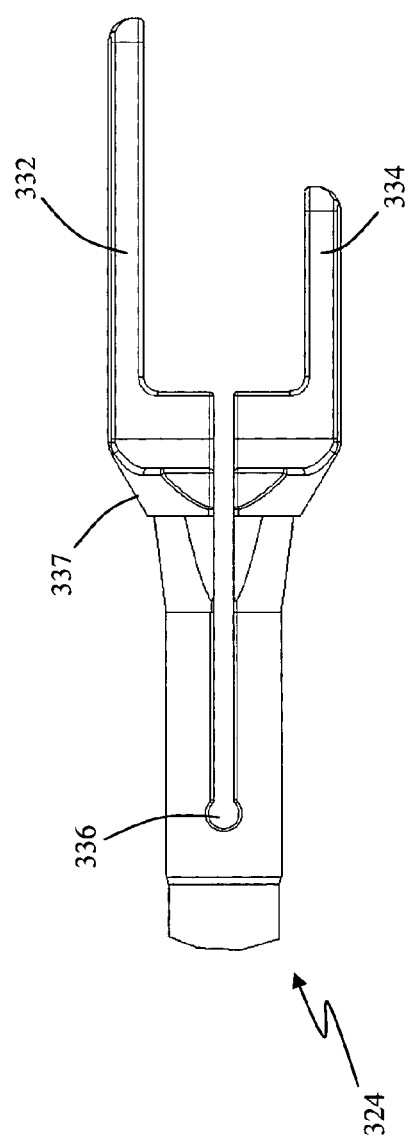
FIG. 16C is a detailed top view diagram of an exemplary 11 mm wide straight implant insertion tool fork distal end in accordance with the present invention.
Figure 16D:
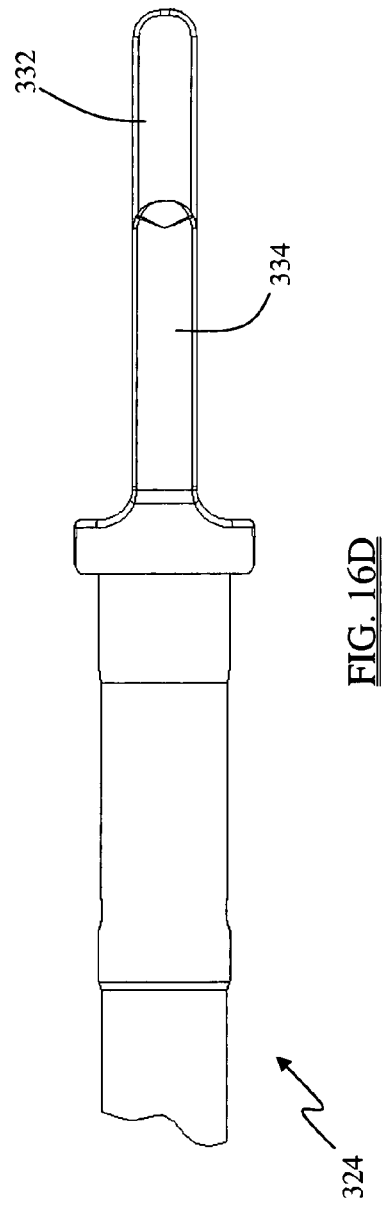
FIG. 16D is a detailed side view diagram of an exemplary 11 mm wide straight implant insertion tool fork distal end in accordance with the present invention.

FIGS. 14-16F are line drawings of an exemplary embodiment of an 11 mm wide straight implant inserter 300 in accordance with the present invention. FIG. 14 is an isometric line drawing of the 11 mm wide straight inserter in its two parts: the collar 310 and fork 320. FIG. 15A is a top view line drawing of the 11 mm wide implant inserter 300 and FIG. 15B is a side view of the line drawing of the 11 mm wide implant inserter 300. FIGS. 16A-16F are line drawings of the exemplary 11 mm wide implant fork 320. FIG. 16A is a side view line drawing of the fork 320 that, in one embodiment, has an overall length of about 12.40 inches and a distal end 324 length of about 1.035 inches. FIG. 16B is a top view line drawing of the fork 320, FIG. 16C is a top view line drawing of the distal end 324 of fork 320, FIG. 16D is a side view line drawing of the distal end 324 of fork 320, and FIG. 16F is an end view line drawing of the distal end 324 of fork 320. FIG. 16E is a side view line drawing of the tool engaging proximal end 326 of the fork 320.

Figure 17:
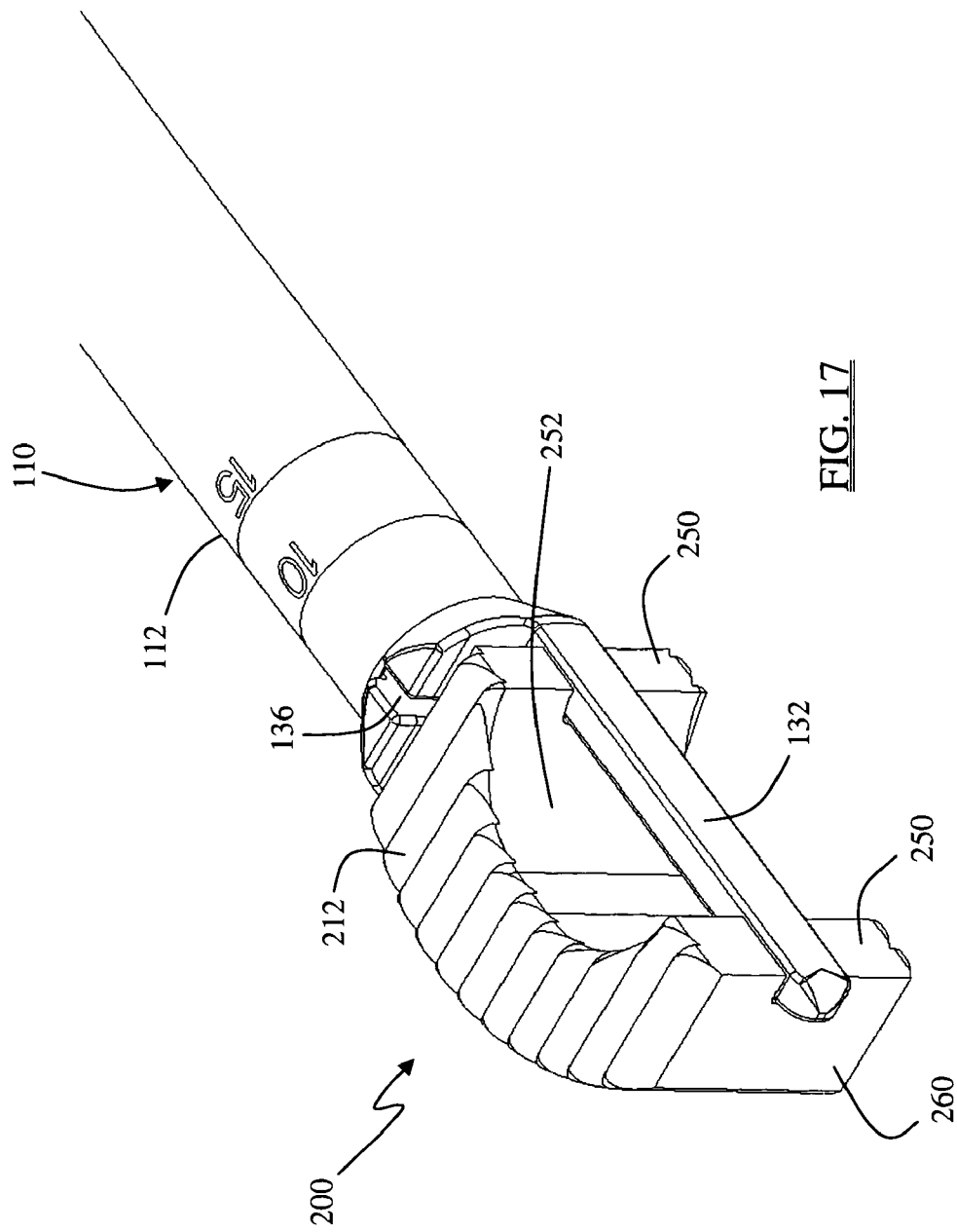
FIG. 17 is an isometric line diagram view of an exemplary 11 mm wide straight implant insertion tool distal end gripping an exemplary 11 mm wide, 20 mm long implant in accordance with one embodiment of the present invention.
Figure 18:
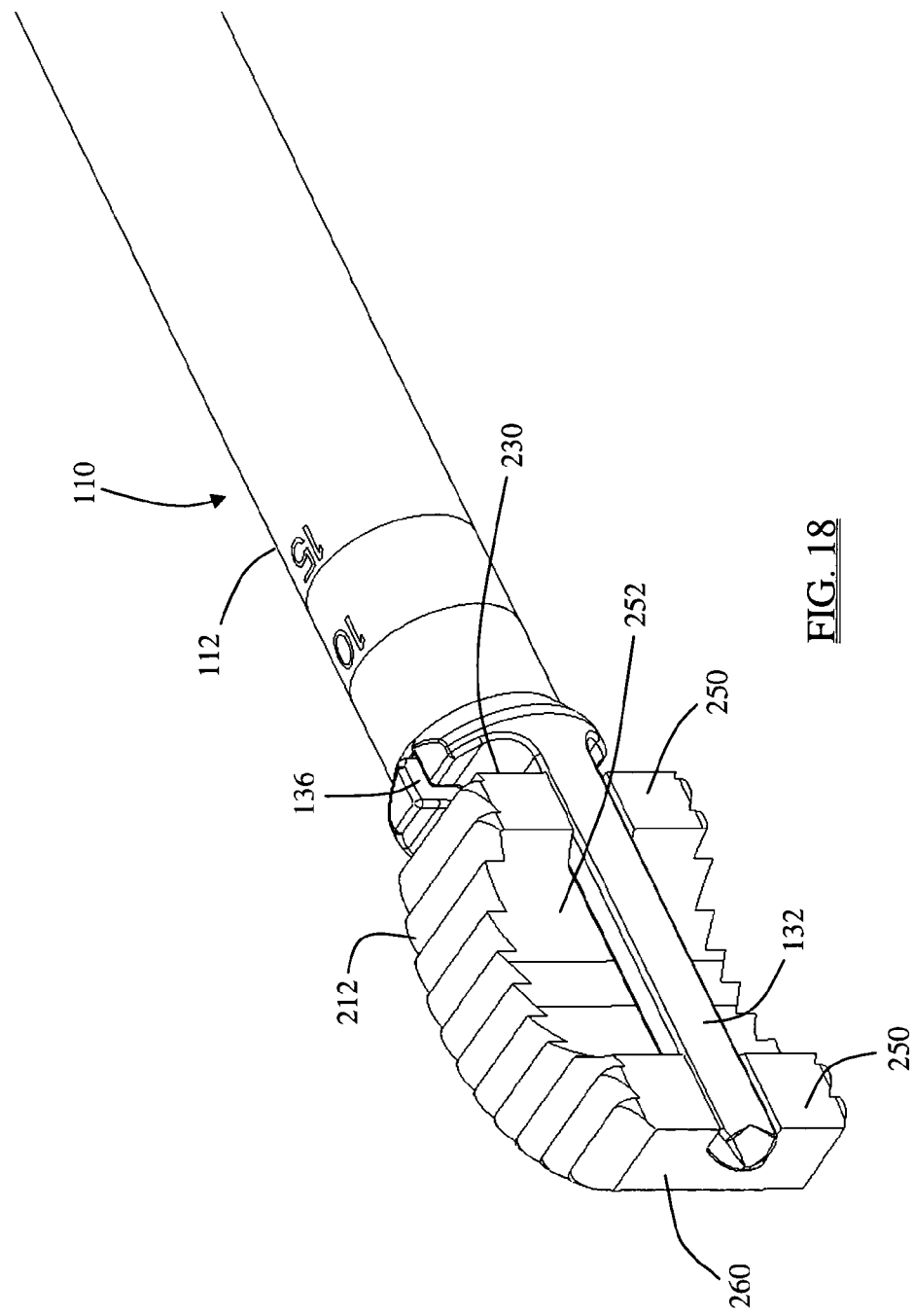
FIG. 18 is an isometric line diagram of an exemplary 9 mm wide straight implant insertion tool distal end gripping an exemplary 9 mm wide, 20 mm long implant in accordance with one embodiment of the present invention.
Figure 19:
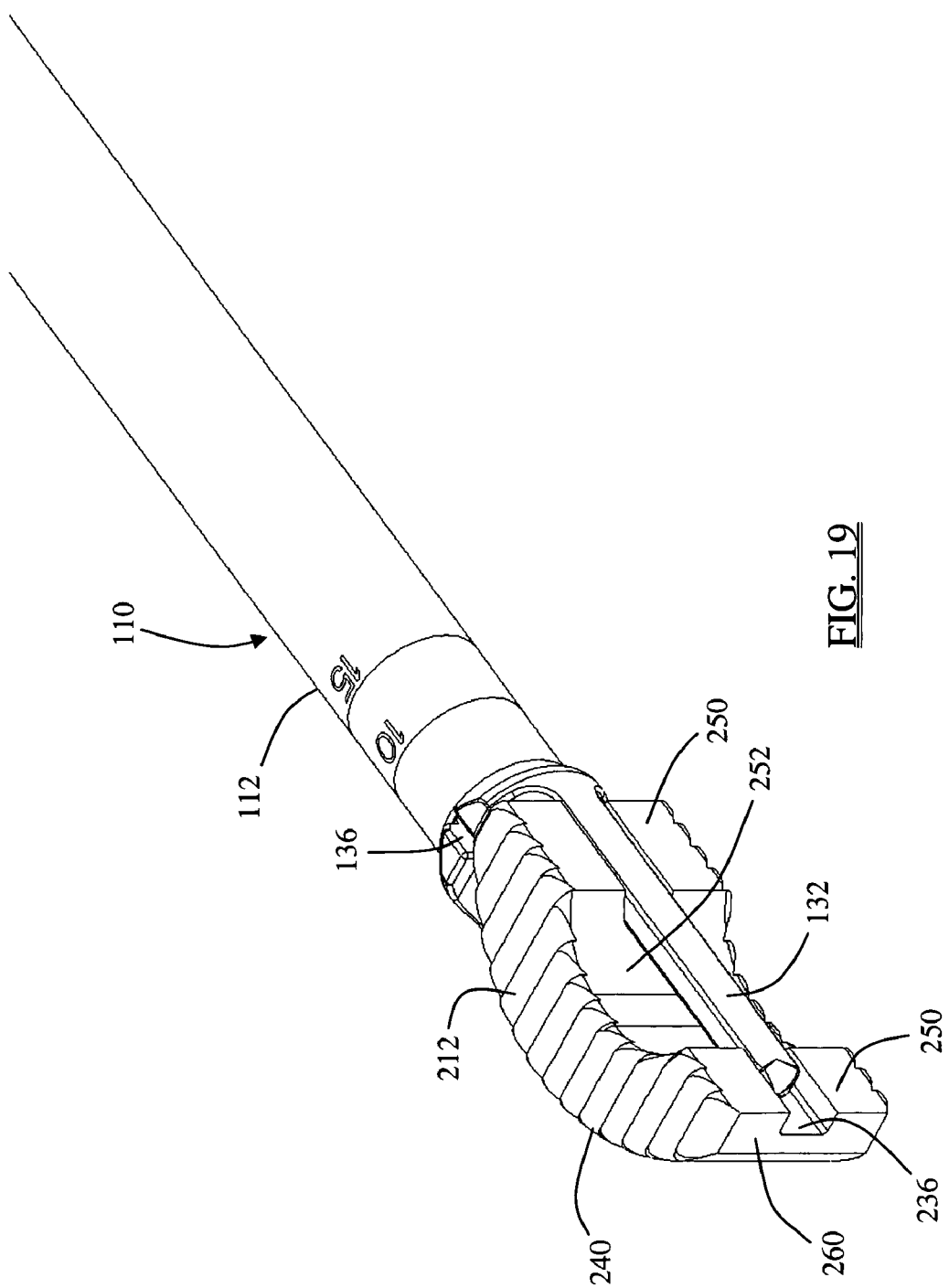
FIG. 19 is an isometric line diagram of an exemplary 9 mm wide implant insertion tool distal end gripping an exemplary 9 mm wide, 25 mm long implant in accordance with one embodiment of the present invention.
Figure 20:
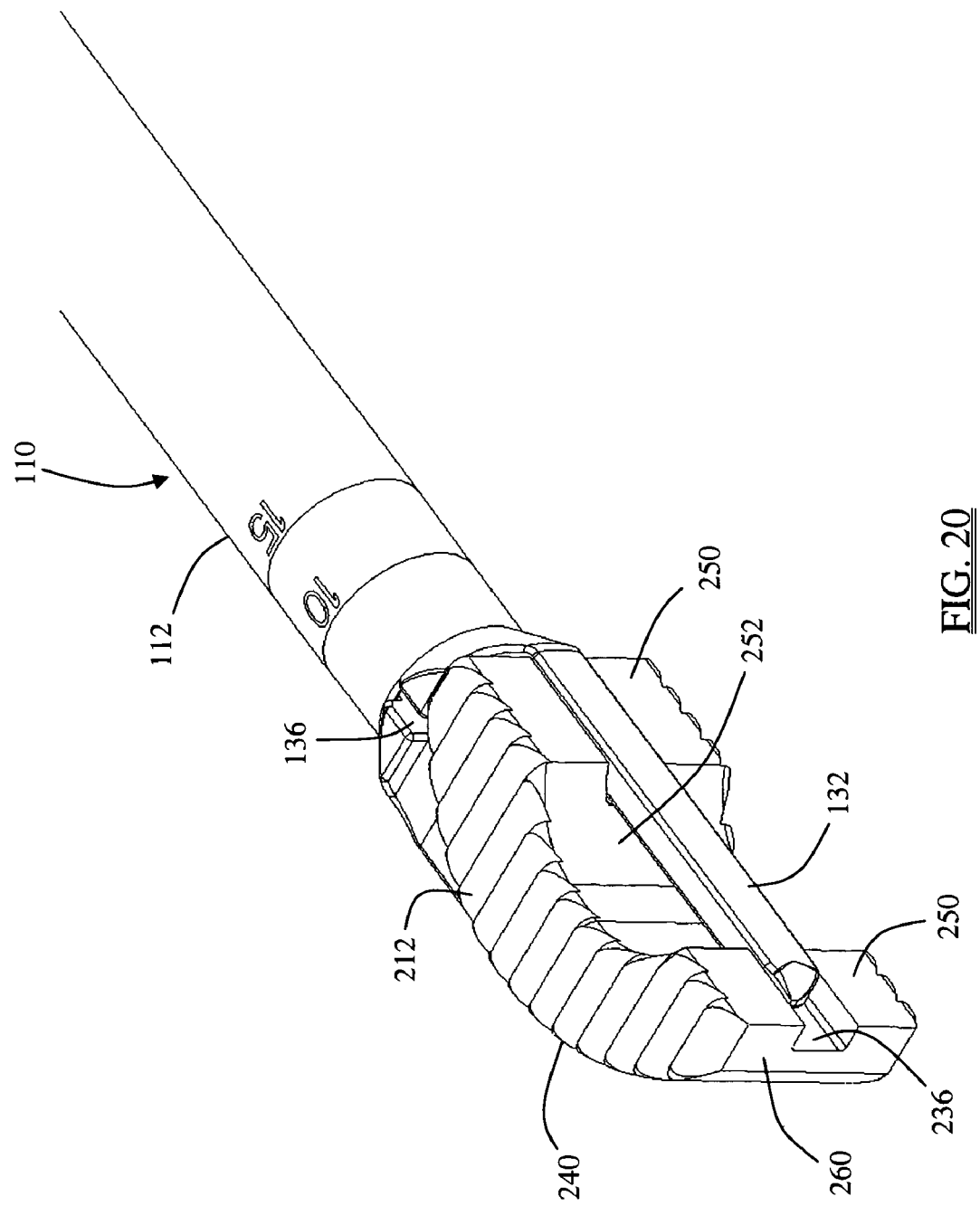
FIG. 20 is an isometric line diagram of an exemplary 11 mm wide implant insertion tool distal end gripping an exemplary 11 mm wide, 25 mm long implant in accordance with one embodiment of the present invention.

FIGS. 17-20 are diagrams of the exemplary 9 and 11 mm wide implant inserter 100 gripping one of the 20 mm and 25 mm long implants 200. FIG. 17 is an isometric line drawing of an exemplary 11 mm wide implant inserter 100 gripping an exemplary 20 mm long implant 200. As shown in these figures, the first prong 132 extends beyond implant end 260. FIG. 18 is an isometric line drawing of an exemplary 9 mm wide implant inserter 100 gripping an exemplary 20 mm long implant 200. FIG. 19 is an isometric line drawing of an exemplary 9 mm wide implant inserter 100 gripping an exemplary 25 mm long implant 200. As shown in these figures, the implant end 260 extends slightly beyond the first prong 132. FIG. 20 is an isometric line drawing of an exemplary 11 mm wide implant inserter 100 gripping an exemplary 25 mm long implant 200.

According to a still further embodiment of the present invention, the various devices described above may be provided with color-coding to facilitate ease-of-use for the surgeon. More specifically, all instruments and implants of a particular size may be provided with specific graphical and/or colored indicia such that the surgeon will know, simply by referring to the colored indicia, which instrument or implant he or she should employ from among the tray of instruments containing the instruments of the present invention. For example, according to one embodiment of the present invention, the 8 mm height implants and instruments may be designated with a red color, the 10 mm height implants and instruments may be provided with a green color, the 12 mm height implants and instruments may be provided with a gold or yellow color, and the 14 mm height implants and instruments may be provided with a blue color. The articles suitable for color-coding according to this feature of the present invention include, but are not necessarily limited to, devices for sizing the disc space to determine what size implant should be inserted, the implant packaging, broaches, and implant inserters.

FIGS. 21-26 illustrate in greater detail a preferred embodiment of the fusion procedure according to the present invention. Once the patient has been prepared for surgery, an incision may be made on the patient's skin at location posterolateral to the desired implant location. Then a trocar or other instrument may be advanced to the annulus of the disc between the vertebrae 10, 20 of interest. A cannula or similar device may then be advanced over the trocar to engage the disc annulus. At this point a clinician may prefer to use a surgical retractor 400 to create an operating corridor 402 through which to insert the implant 200. If necessary, a clinician may perform an annulotomy to remove a section of the annulus and a discectomy thereafter to remove a portion of the disc where the implant 200 is to be placed. Further, the clinician may partially decorticate the endplates of the vertebrae 10, 20.

Figure 21A:
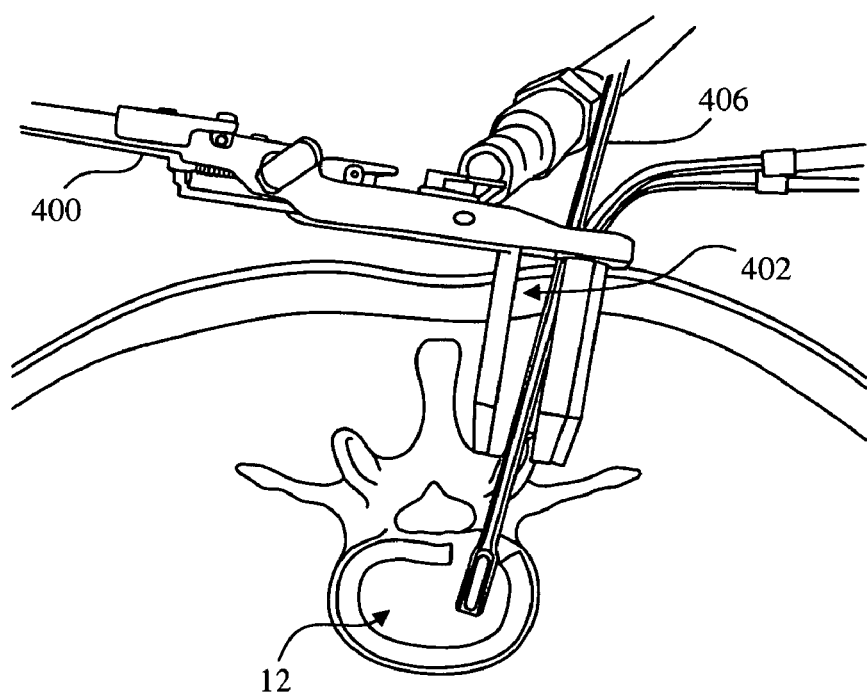
FIG. 21A is a cross-sectional view of an in vivo spinal surgical procedure according to one embodiment of the present invention, illustrating in particular the use of a disc cutter to clear disc material from intradiscal space.
Figure 21B:
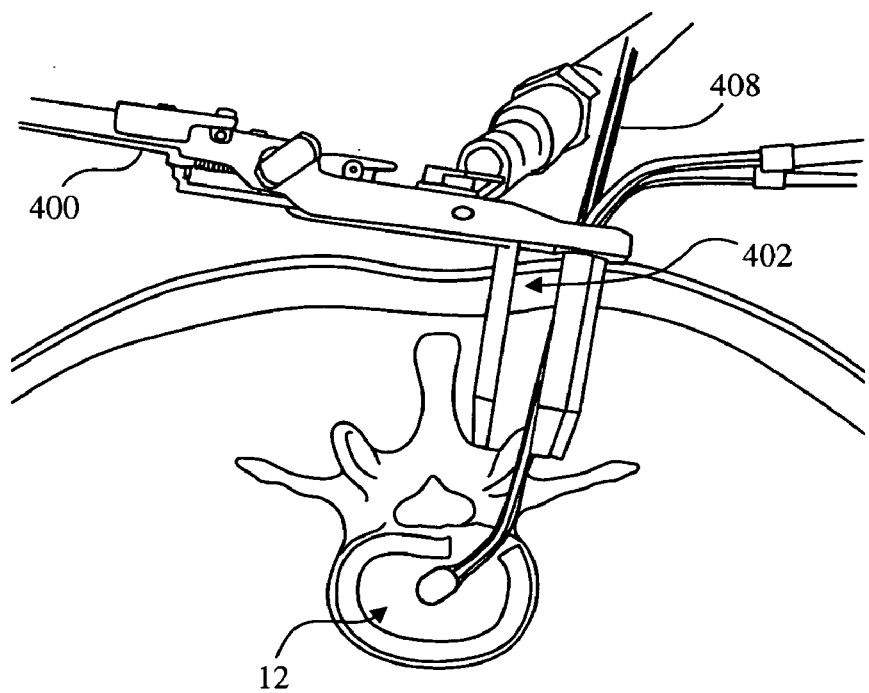
FIG. 21B is a cross-sectional view of an in vivo spinal surgical procedure according to one embodiment of the present invention, illustrating in particular the use of a curette to clear disc material from intradiscal space.
Figure 21C:
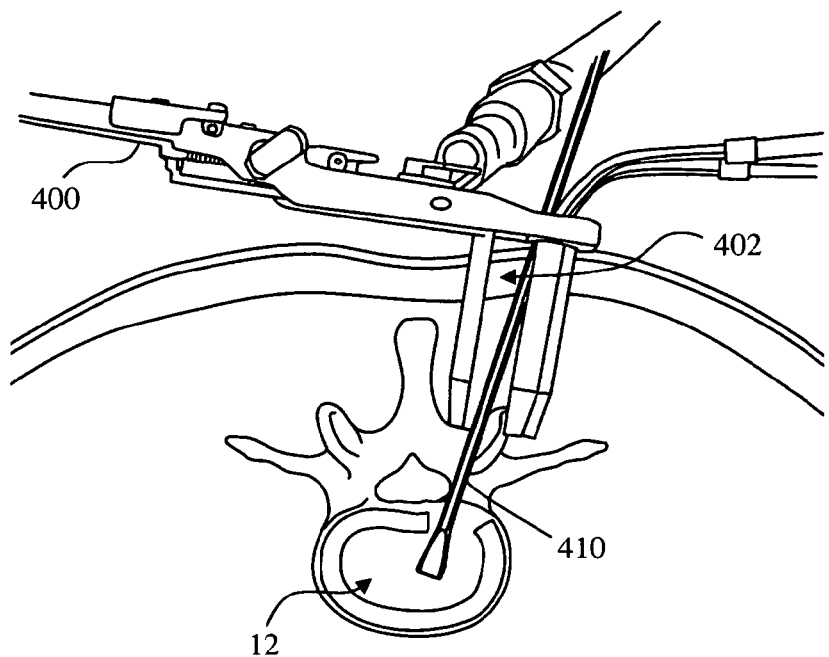
FIG. 21C is a cross-sectional view of an in vivo spinal surgical procedure according to one embodiment of the present invention, illustrating in particular the use of a scraper to clear disc material from intradiscal space.
Figure 21D:
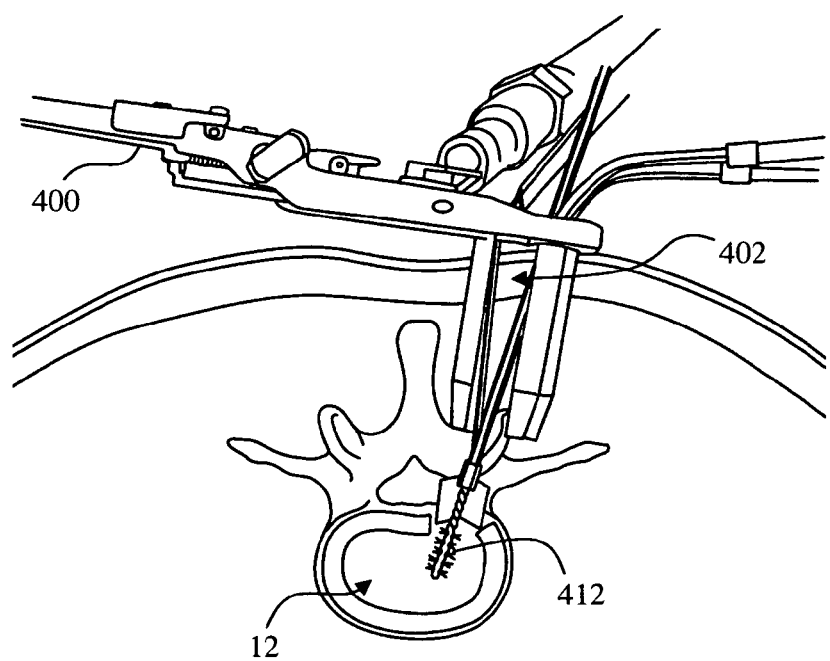
FIG. 21D is a cross-sectional view of an in vivo spinal surgical procedure according to one embodiment of the present invention, illustrating in particular the use of a disc brush to clear disc material from intradiscal space.
Figure 21E:
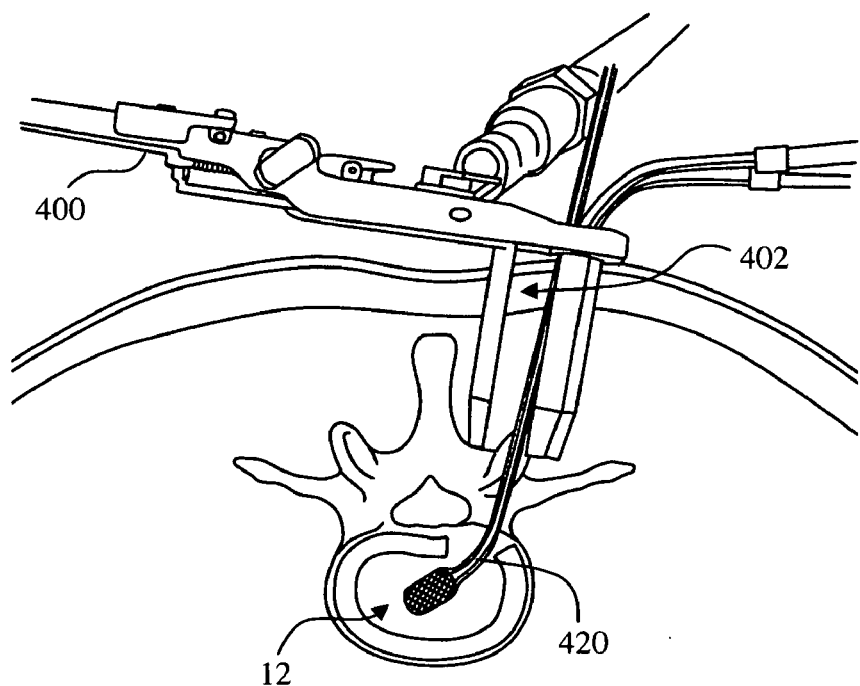
FIG. 21E is a cross-sectional view of an in vivo spinal surgical procedure according to one embodiment of the present invention, illustrating in particular the use of a rasp to clear disc material from intradiscal space.

FIGS. 21A-21E illustrate an exemplary set of steps that may be taken to clean out the disc space 12 prior to insertion of implant 200. FIG. 21A depicts the use of a disc cutter 406 to remove disc material. To accomplish this, disc cutter 406 is employed with a rotating motion, and disc material is cut and loosened from the endplates of vertebrae 10, 20. Cut or loosened disc material is removed by removing the disc utter 406. FIG. 21B illustrates the use of a curette 408 to further remove excess disc material and cartilage from the disc space 12. FIG. 21C depicts the use of a scraper 410 to further remove disc material and cartilage from the endplates of vertebrae 10, 20. FIG. 21D shows the use of a disc brush 412 to still further remove excess disc material. FIG. 21E illustrates the use of a rasp 420 in an optional final step in preparing the endplates. At some point during this procedure, the clinician may distract vertebrae 10, 20 to expand the disc space to a desired height. Based on the distraction height and the size of the vertebrae 10, 20, the clinician may select a suitably dimensioned implant 200. The implant is then placed between the prongs 132, 134 located on the distal end 124 of inserter 100. The prongs 132, 134 are then compressed by rotating the sleeve 112 via grip 114 to securely engage the implant 200, as described above.

Figure 22A:
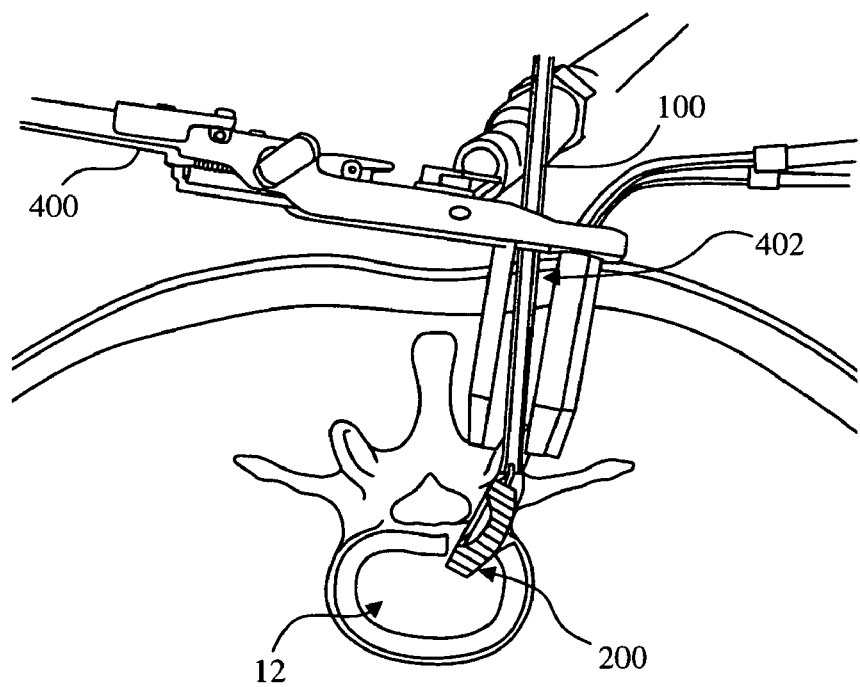
FIGS. 22A-22B are cross-sectional views of an in vivo spinal surgical procedure according to one embodiment of the present invention, illustrating in particular the insertion of an implant into the disc space using an angled inserter.
Figure 22B:
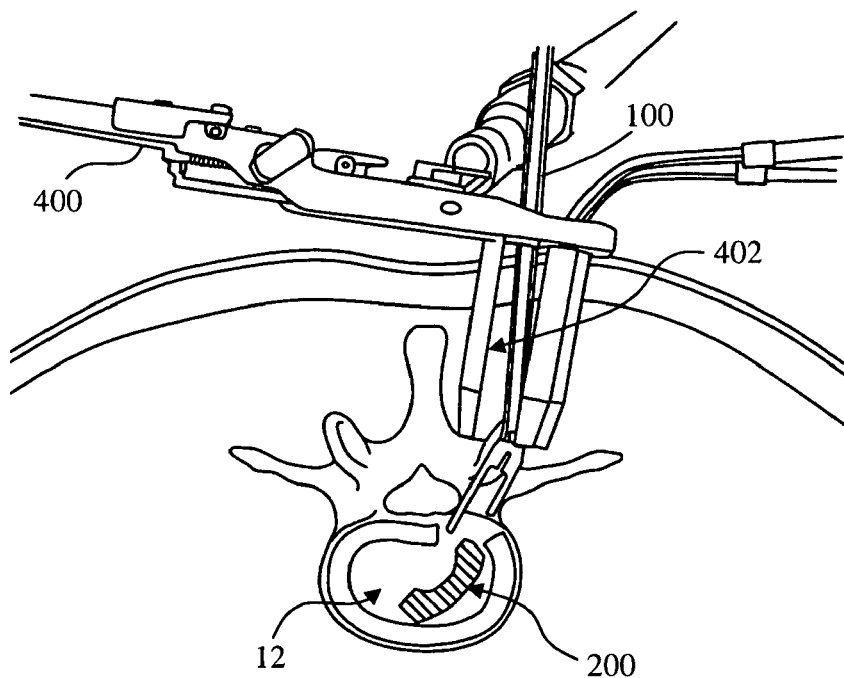
Figure 23A:
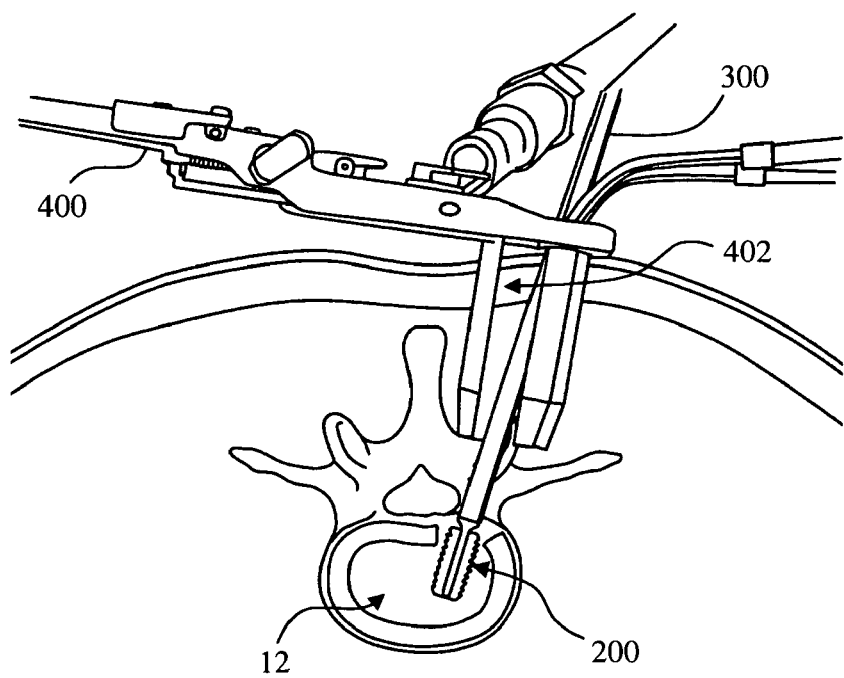
FIGS. 23A-23B are cross-sectional views of an in vivo spinal surgical procedure according to one embodiment of the present invention, illustrating in particular the insertion of an implant into the disc space using a straight inserter.
Figure 23B:
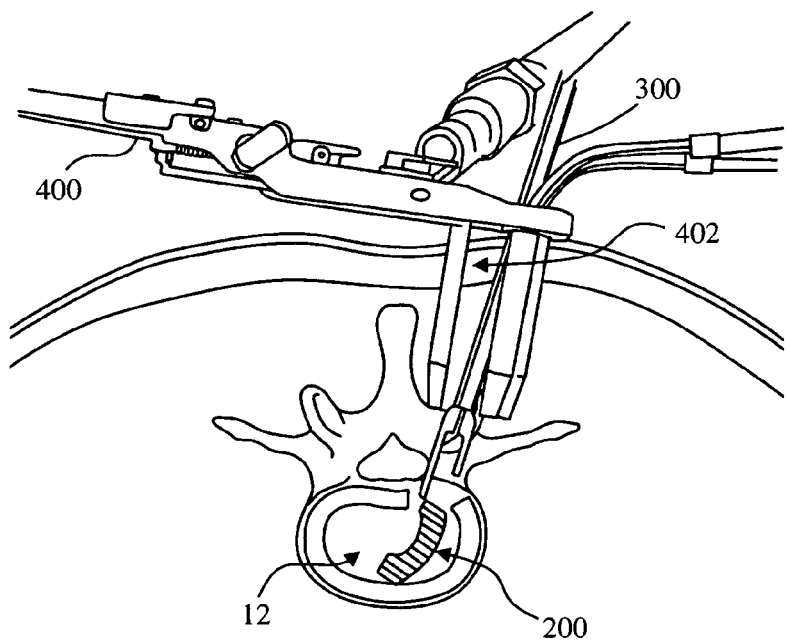
Figure 24:
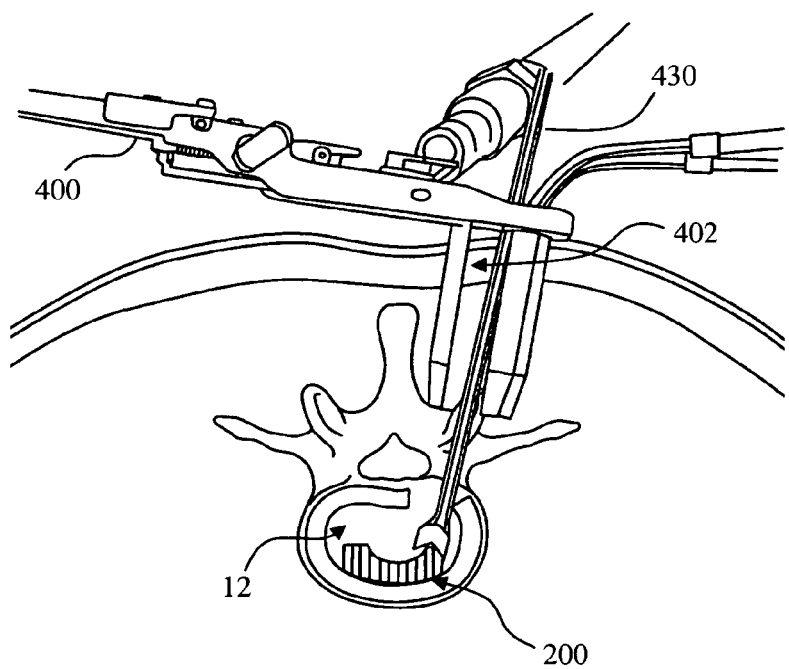
FIG. 24 is a cross-sectional view of an in vivo spinal surgical procedure according to one embodiment of the present invention, illustrating in particular the positioning of an implant within the disc space using a straight tamp.
Figure 25:
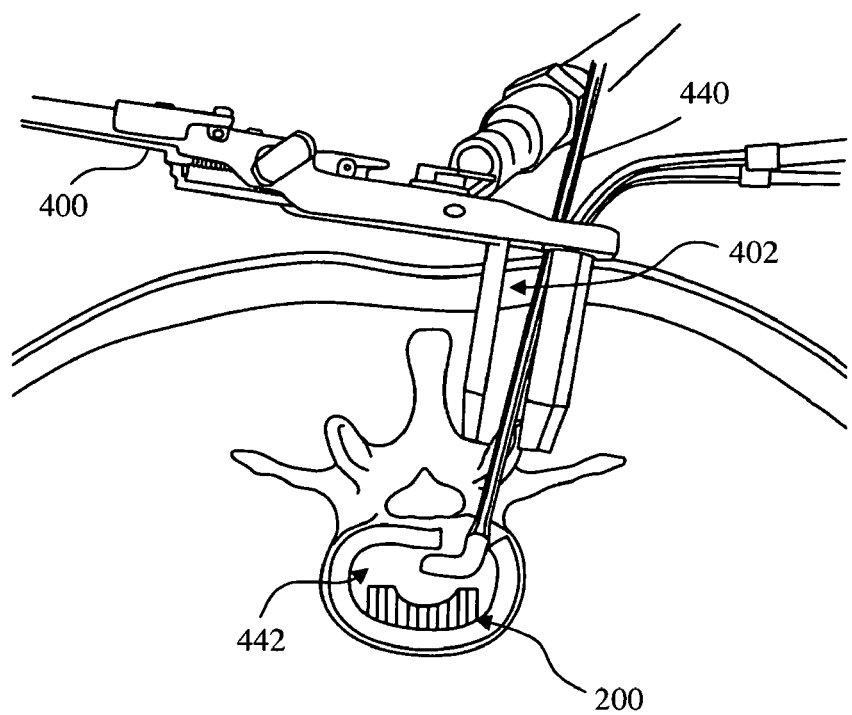
FIG. 25 is a cross-sectional view of an in vivo spinal surgical procedure according to one embodiment of the present invention, illustrating in particular the addition and compaction of graft material within the disc space using a footed tamp.
Figure 26:
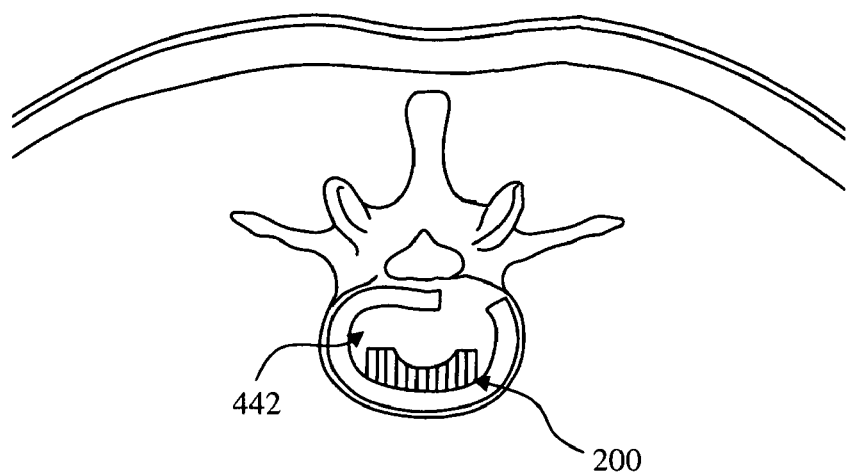
FIG. 26 is a cross-sectional view of an in vivo spinal surgical procedure according to one embodiment of the present invention, illustrating in particular the final positioning of an implant within the disc space after conclusion of the procedure.

As depicted in FIGS. 22A-23B, the clinician may insert the implant 200 into the disc space 12 by passing the inserter 100 through the operative corridor 402 of the retractor 400. As noted, the clinician may take several fluoroscopic pictures to determine the location of the implant 200 within the disc space 12 by observing the location of the distal end 124 of the inserter 100, and in particular the set of prongs 132, 134. According to one embodiment of the present invention, and as shown in FIGS. 22A-22B, angled inserter 100 may be used to insert implant 200 into disc space 12. Alternatively, as shown in FIGS. 23A-23B, straight inserter 300 may be used to insert implant 200 into disc space 12 at a 90-degree rotated orientation. Before releasing the implant 200, the clinician may then rotate the implant 200 to obtain the desired special relationship, as shown in FIG. 23B. Upon placement of the implant 200 in the desired location within the disc space, the clinician may release the implant 200 by rotating the sleeve 112 via the grip 114 counter-clockwise to decompress the set of prongs 132, 134. FIG. 24 illustrates the use of a straight tamp 430 to guide the implant 200 to the desired position. FIG. 25 illustrates the use of a footed tamp 440 used to insert and compress autograft or other fusion-promoting composition (such as bone morphogenic protein) 442 in the disc space 12. FIG. 26 depicts the final positioning of the implant 200 and the allograft material 442 at the close of the procedure according to the present invention. The clinician may remove any distraction means prior to the removal of the inserter 100 so the vertebral endplates of the vertebrae 10, 20 engage with the teeth 112 on the top 210 and bottom 220 of implant 200. Thereafter, the inserter 100 may be withdrawn, the annulotomy closed, the retractor 400 removed, and the incision closed.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein. For example, the exemplary inserter 100 may be modified to handle implants having widths other than 9 and 11 mm. It is contemplated that spinal implants according to the present invention may have any width suitable for use in an intradiscal space. By way of example only, 14 mm wide implant inserter may be used in accordance with the present invention to insert a 14 mm wide spinal implant.

What is claimed is:
1. A system for performing transforaminal lumbar interbody fusion comprising:
 an inserter having a proximal end, a distal end including a distal engagement region, and an elongated shaft extending between said proximal end and said distal engagement region, said shaft defining a first axis extending longitudinally through the center of the shaft, said distal engagement region comprising first and second generally parallel elongated engagement members capable of being biased towards one another and extending distally away from said distal engagement region opposite said shaft, said first engagement member defining a second axis extending longitudinally therethrough, said second engagement member defining a third axis extending longitudinally therethrough, said first and said second engagement members arranged such that said second and third axes are generally parallel to one another and said second engagement member being bent away from said shaft such that said third axis is disposed in an obtuse angular relationship with said first axis and wherein said second and third axes are coplanar with said first axis; and an implant having a top surface, a bottom surface, a first end, a second end, and first and second sides extending between the first and second ends and the top and bottom surfaces, said first side and second side including at least one groove dimensioned to receive at least a part of said generally parallel engagement members.

2. The system of claim 1 and further, wherein at least one of said top and bottom surfaces of said implant include anti-migration features to prevent the implant from migrating once positioned within an intervertebral space.

3. The system of claim 2 and further, wherein said anti-migration features are teeth formed on at least one of said top and bottom surfaces of said implant.

4. The system of claim 1 and further, wherein said first side surface is generally concave.

5. The system of claim 1 and further, wherein said second side surface is generally convex.

6. The system of claim 1 and further, wherein said implant is introduced into a disc space in a unilateral fashion after removing at least a portion of a facet joint on one side of a patient's spine.

7. The system of claim 1 and further, wherein said inserter includes an elongate element having said generally parallel engagement members at a distal end, and a generally tubular member extending over at least a portion of said elongate element and capable of compressing said generally parallel engagement members towards one another to hold said implant.

8. The system of claim 1, further comprising at least one of a device of preparing said disc space to receive said implant, a device for positioning said implant within said disc space after said implant is released from sad inserter, and a device for packing a fusion-promoting composition within said disc space after said implant has been positioned in said disc space.

9. The system of claim 8 and further, wherein said device for preparing said disc space comprises at least one of a scraper and a broach.

10. The system of claim 8 and further, wherein said device for positioning said implant comprises a tamp device for pushing said implant into a desired position within said disc space.

11. The system of claim 8 and further, wherein said device for packing a fusion-promoting composition comprises a tamp having an enlarged region for packing said fusion-promoting compositions into said disc space.

12. The system of claim 1 and further, wherein said inserter includes color-coded indicia corresponding to a particular size of said implant to be employed with said inserter.

13. The system of claim 12 and further, wherein said implant is provided in a color-coded package, wherein said color-coding corresponds to said inserter.

14. The system of claim 1, further comprising a minimally invasive access system for establishing an access corridor to said disc space, through which said inserter passes said implant into said disc space.

15. The system of claim 14 and further, wherein said minimally invasive access system comprises a multi-blade retractor which establishes a unilateral access corridor between the skin of said patient and said disc space.

16. The system of claim 15 and further, wherein said minimally invasive access system comprises a 3-blade retractor system.

17. A method for performing transforaminal lumbar interbody fusion comprising the steps of:

(a) providing an inserter having a proximal end, a distal end including a distal engagement region, and an elongated shaft extending between said proximal end and said distal engagement region, said shaft defining a first axis extending longitudinally through the center of the shaft, said distal engagement region comprising first and second generally parallel elongated engagement members capable of being biased towards one another and extending distally away from said distal engagement region opposite said shaft, said first engagement member defining a second axis extending longitudinally therethrough, said second engagement member defining a third axis extending longitudinally therethrough, said first and second engagement members arranged such that said second and third axes are generally parallel to one another and said second engagement member being bent away from said shaft such that said third axis is disposed in an obtuse angular relationship with said first axis, and wherein said second and third axes are coplanar with said first axis;

(b) providing an implant having a top surface, a bottom surface, a first end, a second end, and first and second sides extending between the first and second ends and the top and bottom surfaces, said first side and second side including at least one groove dimensioned to receive at least a part of said generally parallel engagement members;

(c) positioning said implant within said generally parallel engagement members of said inserter such that said grooves receive said pair of generally parallel engagement members;

(d) biasing said generally parallel engagement members such that said inserter holds said implant;

(e) introducing said generally parallel engagement members such that said inserter holds said implant;

(e) introducing said implant through a unilateral access into a disc space;

(f) releasing said implant from said inserter; and (g) positioning said implant in a desired position within said disc space.

* * * * *